US005498537A

United States Patent [19]
Bresler et al.

[11] Patent Number: 5,498,537
[45] Date of Patent: Mar. 12, 1996

[54] SERUM-FREE PRODUCTION OF PACKAGED VIRAL VECTOR

[75] Inventors: Herbert S. Bresler, Silver Spring; Richard A. Knazek, Mount Airy, both of Md.

[73] Assignee: Cellco, Inc., Germantown, Md.

[21] Appl. No.: 208,520

[22] Filed: Mar. 9, 1994

[51] Int. Cl.$^6$ .............................. C12N 5/10; C12N 7/00; C12N 7/01

[52] U.S. Cl. .................................. 435/235.1; 435/240.2; 435/240.242

[58] Field of Search ................................ 435/235.1, 239, 435/240.31, 240.242, 320.1

[56] References Cited

U.S. PATENT DOCUMENTS

| | | | |
|---|---|---|---|
| 3,821,087 | 6/1974 | Knazek et al. | 195/127 |
| 4,301,249 | 11/1981 | Markus et al. | 435/235 |
| 4,301,250 | 11/1981 | McAleer et al. | 435/241 |
| 4,416,986 | 11/1983 | Markus et al. | 435/68 |
| 4,546,083 | 10/1985 | Meyers et al. | 435/240 |
| 4,686,098 | 8/1987 | Kopchick et al. | 424/424 |
| 4,816,401 | 3/1989 | Taupier | 435/240.31 |
| 4,861,719 | 8/1989 | Miller | 435/236 |
| 4,868,116 | 9/1989 | Morgan et al. | 435/240.2 |

FOREIGN PATENT DOCUMENTS

90/01870  3/1990  WIPO .............................. C12N 15/00

OTHER PUBLICATIONS

Betsholtz et. al. (1984) J. Cell. Physiol. 118(2), 203–210.
Bodo et. al. (1990) Cell. Mol. Biol. 36(6), 673–688.
Knazek et. al. (1990) J. Immunol. Metn., pp. 29–37.
Kumar et. al. (1991) Exper. Cell Res. 193, 398–404.
Kotani, Hitoshi et al., "Improved Methods of Retroviral Vector Transduction and Production for Gene Therapy", *Human Gene Therapy* 5:19–28 (1994).
Anderson, W. French, "Prospects for Human Gene Therapy", *Science* 226:401–408 (1984).
Barnes, David et al., "Methods for Growth of Cultured Cells in Serum–Free Medium", *Anal. Biochem.* 102:255–270 (1980).
Bender, Michael A. et al., "Evidence that the Packaging Signal of Moloney Murine Leukemia Virus Extends into the gag Region", *J. Virology* 61:1639–1646 (1987).

Hock, Randy A. et al., "Expression of Human Adenosine Deaminase From Various Strong Promoters After Gene Transfer Into Hematopoietic Cell Lines", *Blood* 74:876–881 (1989).
Mann, Richard et al., "Construction of a Retrovirus Packaging Mutant and Its Use to Produce Helper–Free Defective Retrovirus", *Cell* 33:153–159 (1983).
Miller, A. Dusty et al., "Improved Retroviral Vectors for Gene Transfer and Expression", *BioTechniques* 7:980–990 (1989).
Miller, A. Dusty et al., "Design of Retrovirus Vectors for Transfer and Expression of the Human β–Globin Gene", *J. Virology* 62:4337–4345 (1988).
Miller, A. Dusty et al., "Transfer of Genes into Human Somatic Cells Using Retrovirus Vectors", *Cold Spring Harbor Symp. Quant. Biol.* vol. LI:1013–1019 (1986).
Miller, A. Dusty et al., "Redesign of Retrovirus Packaging Cell Lines To Avoid Recombination Leading to Helper Virus Production", *Mol. Cell. Biol.* 6:2895–2902 (1986).
Pironin, Martine et al., "Growth in Serum–Free Medium of NIH3T3 Cells Transformed By The EJ–II–ras Oncogene: Evidence for Multiple Autocrine Growth Factors", *Int. J. Cancer* 514:980–988 (1992).
St. Louis, Daniel et al., "An Alternative Approach to Somatic Cell Gene Therapy", *PNAS USA* 85:3150–3154 (1988).
Stead, Richard B. et al., "Canine Model for Gene Therapy: Inefficient Gene Expression in Dogs Reconstituted With Autologous Marrow Infected With Retroviral Vectors", *Blood* 71:742–747 (1988).
Tsang, R. et al., "Production of HTLV–III Virus in Cells Grown on Artificial Capillaries", Poster Presentation at Bio-Expo 86, Apr. 29, 1986, Boston, MA.
Wolff, Jon A. et al. "Expression of Retrovirally Transduced Genes in Primary Cultures of Adult Rat Hepatocytes", *PNAS USA* 84:3344–3348 (1987).

*Primary Examiner*—Mindy Fleisher
*Assistant Examiner*—David Guzo
*Attorney, Agent, or Firm*—Sterne, Kessler, Goldstein & Fox

[57] ABSTRACT

The application concerns a method for the serum-free production of packaged and infectious vital vectors in an artificial capillary system cartridge. The invention further concerns transducing target cells with the vital vectors. The invention is particularly suitable for producing transduced target cells free of adherent serum proteins.

6 Claims, 5 Drawing Sheets

SERUM-FREE PRODUCTION OF PACKAGED VIRAL VECTOR

FIELD OF THE INVENTION

The invention relates to methods for the serum-free production of high titers of viral vectors in an artificial capillary system cartridge. The invention further relates to methods for infecting target cells at high multiplicity and for producing high concentrations of transduced target cells. The methods are particularly suited for producing transduced target cells free of adherent serum proteins.

BACKGROUND OF THE INVENTION

Genetic Therapy

Genetic therapy is a recent and highly promising addition to the repertoire of treatments for acquired and inherited diseases. It is expected that many congenital genetic abnormalities and acquired diseases will be amenable to treatment by genetic therapy. Genetic therapy can be effected by removing target cells from an afflicted individual, modifying the cells by introducing heterologous DNA that encodes a therapeutically effective product and returning the modified cells to the individual. Eventually it may be possible to introduce the heterologous DNA directly into cells in vivo (e.g., endothelial cells that line the lungs) without any in vitro manipulation of the target cells.

Diseases that are candidates for such treatment include those that are caused by a missing or defective gene that normally encodes an enzyme, hormone, or other protein. Examples of such diseases include: a severe combined immunodeficiency disorder, which is caused by a defect in the DNA that encodes adenosine deaminase (ADA) (see, e.g., Kredich et al., in *The Metabolic Basis of Inherited Disease* (5th ed.), Stanbury et al., eds., McGraw-Hill, New York (1983), p. 1157); Lesch Nyhan disease, which is caused by a defect in the enzyme hypoxanthine-guanine phosphoribosyl transferase (HGPRT); cystic fibrosis and Duchenne muscular dystrophy for which the respective defective genes have recently been identified; Tay sachs disease; and hemoglobin disorders, such as β-thalassemia. In addition, genetic therapy has been proposed as a means to deliver therapeutic products, such as tumor necrosis factor (TNF) for the treatment cancers and CD4 receptor protein for the treatment of AIDS (see, e.g., PCT International Application No. WO 90/01870).

Genetic therapy involves introducing heterologous DNA into at least some cells of a host organism in a manner such that the products encoded by the heterologous DNA are expressed in the host. Upon introduction into the host cell, the heterologous DNA may be integrated into the genome of the host cells or it may be maintained and replicated as part of an episomal element. The heterologous DNA may encode products that replace or supplement the product of a defective or absent gene or a gene that is normally expressed at low levels or the DNA may encode therapeutic products that are effective for treating a disease. The heterologous DNA is operatively linked to a promoter and/or other transcriptional and translational regulatory elements that are recognized by host cell effect or molecules, such as RNA polymerase II, such that it can be expressed in the host cell. As understanding of the underlying genetic bases for disease increases, it will be possible to refine the methods of genetic therapy so that regulatory controls that operate at the level of gene transcription or translation or that rely on mechanisms, such as feedback inhibition, to control expression of gene products can also be provided to the host cells. For example, the heterologous DNA may also mediate or encode RNA or protein products that mediate expression of a host cell gene or biochemical process. Expression of the heterologous DNA can thereby be fine-tuned to the needs of the afflicted host.

It is also anticipated that numerous means for introducing heterologous DNA into the cells and genomes of individuals will be developed and refined. At the present time, the use of recombinant viral vectors, which are derived from viruses that infect eukaryotic cells, provide the most promising means for effecting genetic therapy. Generally, upon infection of a eukaryotic host, a virus commandeers the transcriptional and translational machinery of the host cell. In order to do so, vital regulatory signals, such as promoters, particularly those recognized early in infection, tend to be highly efficient so that any DNA that is in operative linkage with such promoters and regulatory signals is efficiently expressed at high levels. Eukaryotic viruses have, therefore, been used as vectors for cloning and expression of heterologous DNA in eukaryotic cells.

Recombinant eukaryotic viruses for delivery of heterologous DNA

Eukaryotic viruses from which recombinant vital vectors have been constructed include both DNA viruses, such as SV40, adenovirus, and bovine papilloma virus (see, e.g., Gluzman, Y., ed. Eukaryotic Viral Vectors, Cold Spring Harbor Laboratory, Cold Spring Harbor, N.Y. (1982); Sarver et al., *Mol. Cell Biol.* 1:486 (1981); and U.S. Pat. No. 4,419,446 to Howley), and RNA viruses, retroviruses, such as Moloney murine leukemia virus (MoMLV), mouse mammary tumor virus (MMTV), Rous sarcoma virus (RSV) and other leukemia and tumor viruses (see, e.g., Mann et al., *Cell* 33:153–159 (1983); Miller et al., *Mol. Cell. Biol.*6:2895–2902 (1986); U.S. Pat. No. 4,868,116 to Morgan et al.; U.S. Pat. No. 4,686,091 to Kopchick et al.; and U.S. Pat. No. 4,861,719 to Miller).

Design of retroviral vectors for use in methods of genetic therapy

Retroviral vectors are presently the preferred vectors for genetic therapy (see, e.g., Anderson, *Science* 226:401–409 (1984)) because retroviral infection is highly efficient and retroviral vectors can be readily modified so that heterologous DNA carried by such vectors is stably integrated into the host cell genome. If retroviral vectors could be produced at a sufficiently high concentration, virtually 100% of exposed target cells, cells that are derived from the afflicted host, could be infected and express integrated proviral and heterologous DNA. Upon infection with a retrovirus, and under appropriate conditions, a single copy of a provirus integrates per cell. Proviral integration is not, per se, harmful to the cell. Also, because of the size and mechanism of retroviral integration, it is possible to know precisely what DNA has been integrated. Finally, retroviral vector systems that have a broad host range are readily available.

Retroviruses consist primarily of a protein envelope that encapsulates core proteins and RNA. The RNA of a retrovirus encodes two long terminal repeat sequence (LTRs), which include promoter and enhancer regions and which flank the genome; various regulatory signals that regulate transcription, including the CAP site and polyadenylation signals, and that regulate reverse transcription and proviral replication; structural genes including the env gene, which encodes the envelope proteins, the gag gene, which encodes viral core proteins, and the pol gene, which encodes the reverse transcriptase. The retroviral RNA also includes signal sequences, such as the tRNA binding site (the replication initiation site for minus DNA strand synthesis), the replication site for plus DNA strand synthesis, and the packaging signal, the psi site.

Retroviral envelope proteins include regions that recognize and specifically bind to mammalian cell surface receptors. Some retroviral envelope proteins only bind to a restricted range of host cells; viruses encapsulated in such envelopes are said to have an ecotropic host range. Other envelope proteins bind to a variety of mammalian cells; viruses encapsulated in such envelopes are said to have an amphotropic host range. Upon specific recognition and binding to host cell receptors, the virus enters the cell. The retroviral reverse transcriptase is translated and the virus is reverse transcribed into a DNA intermediate, referred to as a provirus, which integrates into chromosomal DNA. Proviral DNA can also be replicated and packaged into infectious virions.

Elements for retroviral replication are divided into those that act in cis and those that act in trans. Trans-acting factors include the vital proteins that are necessary for encapsidation, binding and entry of the virus into a target cell, reverse transcription, and integration of the reverse transcribed DNA into the target cell genome. Cis-acting factors, such as the packaging signal, include those that interact with the trans-acting proteins and other proteins during viral replication (see, e.g., Coffin, J. in RNA Tumor Viruses, vol. 2, R. Weiss et al., eds, Cold Spring Harbor Laboratory, Cold Spring Harbor, N.Y. (1985), pp. 17–74).

Some of the cis- and trans-acting functions can be deleted from a retrovirus and, if properly combined, provided separately. A virus that has some or all of the trans-acting functions deleted is replication incompetent, but, if missing functions are provided, such as by co-transfection with a helper virus containing the necessary functions, packaged defective infectious viral particles can be produced. Alternatively, missing functions can be provided by a cell line, a packaging cell line, that has been modified by stable incorporation of such functions in its genome. Because certain functions can be deleted and provided by way of a helper virus or as part of a packaging cell line, retroviral vectors for delivering heterologous DNA, which is then stably integrated into host cell DNA can be constructed. In addition, by careful design of packaging cell lines and retroviral vectors, it is possible to package infectious replication incompetent retroviral vectors without producing helper virus and thereby provide vectors for integrating DNA into a host cell genome without the concomitant risk of recombinational events between the vector and helper virus that could lead to the production of infectious retroviral particles.

Retroviral vectors are constructed by preparing DNA copies of the retroviral RNA and deleting all or parts of the env, pol and gag genes. Heterologous DNA is inserted in place of the deleted genes under the control of the endogenous heterologous promoter or other promoter recognized by a host cell RNA polymerase II, or the retroviral 5' LTR. Retroviral vectors, thus, do not include genes for replication. When they are transduced, in the absence of helper virus, into cells that do not include such retroviral sequences, the retroviral vectors cannot replicate and, if properly constructed, they are stably incorporated into the host cell genome. In addition to the LTR sequences and other cis-acting regulatory sequences, retroviral vectors generally also include splice donor and acceptor sites and a selective marker gene, such as the bacterial gene, neo, which encodes neomycin phosphotransferase, which confers resistance to certain antibiotics, under the control of an appropriate eukaryotic promoter.

The host range of the packaged retroviral vector can be controlled by selection of the env gene that is incorporated into the packaging cell line. If an amphotropic host range is desired, then the vector is packaged in a packaging cell line that includes env sequences derived from a retrovirus that has an amphotropic host range. For example, MoMLV (see, e.g., Mann et al., *Cell* 33:153–159 (1983); and Miller et al., *Mol. Cell. Biol.* 6:2895–2902 (1986)) is an amphotropic retrovirus; its env protein binds to receptors present on most human cells.

Since retroviral vectors do not replicate in the target host cell, retroviral vectors are replicated and packaged in cell lines that include DNA that encodes functions, absent in the vector, that are necessary for packaging and replication. Because of the ease with which retroviruses integrate and excise from chromosomal DNA and undergo recombination, recombination between the DNA derived from the vector and DNA in the packaging cell line may result in production of packaged, replication competent viruses and/or helper viruses, which encode functions necessary for viral replication. Upon transduction into a target host cell, in the presence of helper viruses, recombination can result in the production of infectious retroviral particles in the host cells. Consequently, for clinical use, not only must retroviral vectors be replication incompetent, the packaging cell line and vector must be designed so that there is virtually no possibility of recombination that could lead to the production of replication competent or helper viruses. This is achieved by carefully designing both the vector and the packaging cell line to include deletions and mutations that would render it highly improbable or impossible for any undesirable recombinational events between the retroviral vector and packaging cell line (see, e.g., Mann et al., *Cell* 33:153–159 (1983); Miller et al., *Mol. Cell. Biol.* 6:2895–2902 (1986) and *Mol. Cell. Biol.* 5:431 (1985); and U.S. Pat. No. 4,861,719 to Miller). There is, however, the minute possibility of undesirable recombinational events between the vector and sequences carried on the host cell genome that could result in the production of helper virus or activation of cellular oncogenes. These risks are, however, minute and retroviral vectors have been designed that render the probability of such occurrences insignificant.

Design of packaging cell lines for production of clinically useful recombinant retroviral vectors Manipulation of the viral genome has, thus, permitted construction of retrovirus-packaging cell lines that can produce relatively large amounts of viral vectors in the absence of both replication-competent virus and helper virus. These cell lines package retroviral vector RNA into virions that are capable of infecting a broad range of target host cells, but, that, after infection of such cells, cannot replicate. Packaging cell lines-contain retrovirus-derived DNA that supplies the necessary gene functions, such as the env gene, for vital packaging. Most such packaging cell lines contain helper virus DNA that has been modified by deletion of the packaging signal. It has been found, however, that packaging cell lines in which only the packaging signal is deleted will produce helper virus at low frequency and also interact with some retroviral vectors to yield replication-competent virus at low levels. Thus, additional mutations are introduced into the retroviral DNA in the packaging cell lines in order to further decrease probability for production of helper virus and/or also replication-competent virus (see, e.g., Miller et al., *Mol. Cell. Biol.* 6:2895–2902 (1986) and U.S. Pat. No. 4,861,719 to Miller).

Packaging cell lines are derived from transformed or immortalized cell lines, such as NIH 3T3 cells, and particularly from NIH 3T3 (TK⁻) cells. A DNA construct, such as a plasmid, containing the retroviral sequences with the desired deletions and mutations and a selective marker, such as the herpes simplex virus (HSV) thymidine kinase (TK) gene are introduced into the cell line, such as the NIH 3T3 TK⁻ cells, and cultured in selective medium. Cells, which grow in the selective medium, are selected and tested for the presence of the necessary packaging functions. Those that produce retroviral vectors and do not produce helper viral are selected and used as packaging cell lines to produce infectious replication-incompetent retroviral vectors.

Target cells and their use in genetic therapy

Suitable target cells for gene transfer are those that readily can be obtained and that persist following transplantation, such as fibroblasts, immune cells, particularly lymphocytes, and epithelial cells (See, e.g., St. Louis et al., *Proc. Natl. Acad. Sci.* 85:315054 (1988); Keller et al., *Nature* 318:149–154 (1985); Miller et al., *J. Virol.* 62:4337–4345 (1988); and Morgan et al., U.S. Pat. No. 4,868,116 (1989)).

The first use of genetic therapy in humans involved tumor infiltrating lymphocytes (TILs) as target cells (see, Rosenberg et al., *New Engl. J. Med.* 9:570–578 (1990)). TILs are a lymphocyte subpopulation that show promise as vehicles for delivery of anti-cancer therapeutics to tumor sites. These lymphocytes infiltrate into tumors, as part of an attempt by the host's immune system to mount an immunological response. TIL cells for use as target cells for genetic therapy can be produced in vitro by incubating resected human tumors, such as kidney, colon or breast tumors, melanomas, and sarcomas in vitro in appropriate tissue culture medium that contains interleukin-2 (IL-2). The IL-2 in the medium results in the expansion and activation of T cells within the tumor, the TIL cells, and the destruction of tumor cells or tissue. After 2–3 weeks in culture, the tumor cells have been destroyed and the culture primarily contains lymphoid cells that have the phenotype of cytolytic T lymphocytes (CTL) (see, e.g., Rosenberg et al., *N. Engl. J. Med.* 319:1676–1680 (1988); Muul et al., *J. Immunol.* 138:989–995 (1987); and Topalian et al., *J. Immunol.* 142:3714–3725 (1989)).

TIL cells also show promise for use in methods of genetic therapy, particularly cancer therapy, (see, e.g. Culliton, "News and Comment" in *Science* 244:14301433 (1989), and Kasid et al., *Proc. Nat'l. Acad. Sci.* 87:473–477 (1990)) because they provide a source of autologous cells that target tumors and that can be modified by the insertions of DNA encoding a desired protein, cultured, and reintroduced into the patient. Recently, TILs containing DNA encoding a bacterial marker gene, neo, which encodes neomycin phosphotransferase, were infused into the veins of melanoma patients in order to track the fate of the TILs after infusion in the patients (see Rosenberg et al., *New Engl. J. Med.* 9:570–578 (1990)). The gene was inserted into a retroviral vector, which was then introduced into a retroviral packaging cell line (Miller et al., *Mol. Cell Biol.* 6:2895–2902 (1986)). The packaging cell line was cultured and yielded packaged defective virions at titers sufficient to transduce TIL cells at a multiplicity of infection of virions to cells of about 1.3 to 2.3. After transduction, the cells were cultured overnight, and, in an effort to increase the number of cells infected, the TILs were again exposed to the virus. Although only 1 to 11% of the cells were transduced, it was possible to locate and identify the infused TIL in the treated patients for at least 64 days.

TILs from patients with advanced melanoma have been modified by insertion of DNA encoding TNF and will be reinfused into the patients in an effort to enhance the anti-tumor activity of the TIL cells.

The first experiment in genetic therapy for the treatment of a genetic disorder, a severe combined immunodeficiency disease, is presently underway. ADA deficiency, which is associated with a severe combined immunodeficiency disease, is a fatal condition because the ADA substrates, deoxyadenosine and adenosine, which are toxic to T and B lymphocytes, accumulate in serum of the affected individual. In the hope of treating this disorder, a retroviral vector containing DNA encoding adenosine deaminase (hereinafter ADA) (Hock et al., *Blood* 74:876–881 (1989)) has been introduced into lymphocytes obtained from a child ADA deficiency.

The retroviral vector was packaged in vitro using a cell line shown to produce relatively high liters of the retrovirus containing the ADA gene without concomitant production of helper virus. Although the titers produced by the packaging cells were relatively high, they were only high enough to infect at a multiplicity of infection of about 1 virion/target lymphocyte, which was sufficient to transduce at most about 10% of exposed target cells after repeated exposures of the target cells to the packaged retroviral vectors. The transduced lymphocytes were then infused into the child. It is hoped that after repeated infusions of similarly transduced lymphocytes that sufficient levels of ADA will be expressed to reduce the concentrations of toxic metabolites and thereby permit development of a normal array of immune cells.

Since lymphocytes have a limited lifespan, infusions of transduced lymphocytes will have to be repeated at regular intervals. For each such infusion lymphocytes will have to be transduced and each transduction will require multiple exposures of the lymphocytes to the packaged retroviral vectors because only relatively low titers of the retroviral vectors can be obtained. Even with as many as six exposures of the lymphocytes to packaged retroviral vectors, only about 10% of the cultured lymphocytes will be transduced. This procedure is, therefore, costly and, unless improved, will not be available for general clinical use.

Because retroviral particles are fragile, they cannot be concentrated by any means known to those of skill in the art. The concentration (transduced cells/total number of target cells×100) and total number of transduced target cells that can be obtained is limited by the liter of the retroviral particles produced by the packaging cell line, which in turn is limited by the concentration of packaged particles that are released into the culture medium bathing the packaging cell line. Generally, only tilers of from $7 \times 10^3$ to $5 \times 10^5$ CFU/ml can be obtained (see, e.g., U.S. Pat. No. 4,861,719 to Miller), which severely limits their usefulness in genetic therapy. In order to transduce sufficient numbers of target cells, however, it is necessary to have titers of at least $10^6$ to $10^7$ CFU/ml) (Miller et al., *J. Virol.* 62:4337–4345 (1988)).

Culture media for supporting growth of fibroblastic cells

It has been generally accepted that successful in vitro culture of virtually all cell types requires culture medium supplemented with serum (Barnes et al., *Analytical Biochemistry* 102:255–270 (1980). Exceptions included the discovery that human lymphoid cells are capable of growing in vitro in the absence of bovine serum (see, e.g., Tsang et al. Poster Presentation at Bio-Expo 86, Apr. 29, 1986, Boston, Mass.). However, in vitro cultures of fibroblastic cells in the absence of serum have generally been unsuccessful. For example, Pironin et al. (*Int. J. Cancer* 51:980–988 (1992)) established that NIH/3T3 cells are unable to grow autonomously in vitro in monolayer culture in the absence of bovine serum. To achieve cellular growth in the absence of bovine serum, Pironin et al. transformed the NIH/3T3 cells with the EJ-H-ras oncogene which apparently caused the secretion of autocrine growth factors.

Similarly, Barnes et al., *Analytical Biochemistry* 102:255–270 (1980), reported that an SV40 virus-transformed BALB 3T3 cell line could be grown in vitro on culture plates in the absence of serum but only if the culture plates were coated with cold-insoluble globulin and if the culture medium included insulin, transferrin and a cis-unsaturated fatty acid such as linoleic acid at a concentration of 3–5 μg/ml. Unfortunately, this concentration of linoleic acid is reported as being toxic if added to the medium alone and thus bovine serum albumin (BSA) must also be added to the medium to act as a lipid carrier. Barnes et al. also reported in vitro growth of BALB 3T3 cells and Swiss 3T3 cells in serum-free medium but only if the medium was supplemented with insulin, transferrin, epidermal growth factor, fibroblast growth factor, and partially purified Gimmel factor and if the culture plates were coated with serum-containing culture medium. Barnes et al. concluded that growth rates in serum-free medium were not as good as growth rates in serum-supplemented medium.

Thus, prior to the present invention, in vitro cultures of fibroblastic cells in the absence of bovine serum have generally been unsuccessful or required transforming the fibroblastic cells with a ras oncogene. This is important since, as discussed above, packaging cell lines have been genetically engineered from certain fibroblastic cell lines (e.g., 3T3 cells). After in vitro culture, cell supernatant from these packaging cell lines contain both packaged recombinant vector and the bovine serum proteins. When target cells (such as lymphocytes) are transduced with the packaged vector, some of the bovine serum proteins will adhere to the target cell surface. In a recent study of lymphocyte transplantation, the investigators reported that recipient patients experienced Type III hypersensitivity reactions due to bovine serum proteins adherent to the infused cells. Thus, there is a need in the art for in vitro culturing methods that allow fibroblastic cellular growth in serum-free medium. The successful in vitro production of high titers of packaged recombinant viral vectors from packaging cell lines cultured in serum-free medium would allow the transduction of target cells which could be infused into a patient without eliciting an adverse immune response. To date, such an in vitro culturing system has not appeared in the literature.

SUMMARY OF THE INVENTION

Methods for producing high titers of recombinant viral vectors by culturing producer cells in serum-free culture medium in a artificial capillary system (ACS) cartridge are provided. In particular, methods for producing sustained and continuous production of a high titer of recombinant eukaryotic viral vectors, particularly recombinant retroviral vectors, by culturing producer cells in serum-free medium in a hollow fiber bioreactor are provided.

By the method of the present invention, high titers of packaged and infectious viral vectors are produced in the serum-free culture medium without the presence of exogenous growth factors such as cytokines or mitogens. Thus, the serum-free culture medium itself is capable of supporting growth of the producer cells.

The producer cells (i.e., packaging cells) secrete high titers of the recombinant viral vectors into serum-free medium contained within the extra capillary space (ECS) of an artificial capillary system (ACS) cartridge. In a preferred embodiment, a packaging cell line containing DNA that is derived from a retroviral vector is cultured in the ACS cartridge. High titers, generally at least about $10^6$ cfu/ml, of infectious packaged retroviral vectors accumulate in the ECS medium. If the ECS medium is harvested and replaced with fresh medium, the producer cell continue to secrete viral vectors at a high rate, generally at least about $10^8$ retroviral particles/ml per day. The ECS medium can be repeatedly harvested and production of recombinant retroviral vectors continues and is sustained at a high level.

The ability to produce high titers of recombinant viral vectors permits the transduction target cells. Thus, the present invention further provides methods for transducing target cells with viral vectors. Transduction occurs by contacting target cells with the ECS medium that contains the infectious viral vectors at a multiplicity of infection that may be as high as 10 cfu/target cell.

Medium from the ECS of the virus-producing hollow fiber bioreactor is pumped either continuously, periodically or intermittently into the ECS of the target cell hollow fiber bioreactor. The circuit also includes reservoir bottles that contain the ECS replacement medium (1) for the virus-producing bioreactor and for collecting the spent ECS medium (2) from the target cell bioreactor Several smaller reservoir bottles (4) are included in the connecting lines between the ECS of the two bioreactors and between the reservoirs (1) and (2). The smaller bottles may be used for sample withdrawal, inoculation, or for displacement of the ECS medium in either bioreactor with sterile air. There are filters (f) on the each of the reservoirs and smaller bottles. Clamps (|x|) are present in the various lines to direct the flow of medium. Connectors ($C_o$), which may be placed in any of the lines, permit removal and replacement of any component of the circuit. An automatic pinch valve, which opens when the peristaltic pump (P) is activated and closes when the pump is not pumping, may also be included in the circuit.

Figure 4:
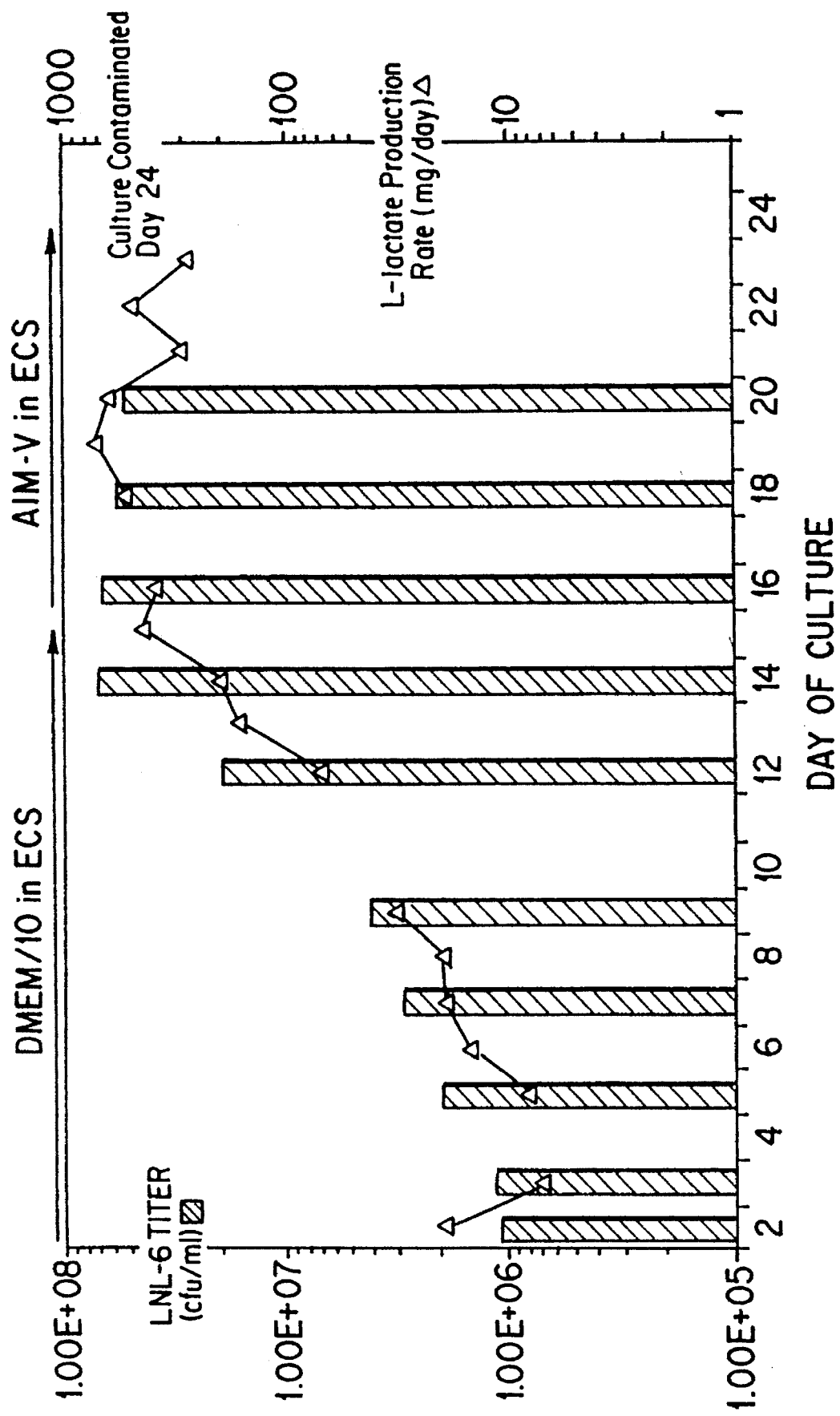

FIG. 4 shows graphically (bar graph) LNL-6 infectivity titers achieved (as assessed by a colony forming assay) when LNL6-packaging cells were cultured in an ACS cartridge (B8) at 34° C. in both serum-containing and serum-free medium. Also shown is the L-lactate production during culture (connected triangles).

Figure 5:
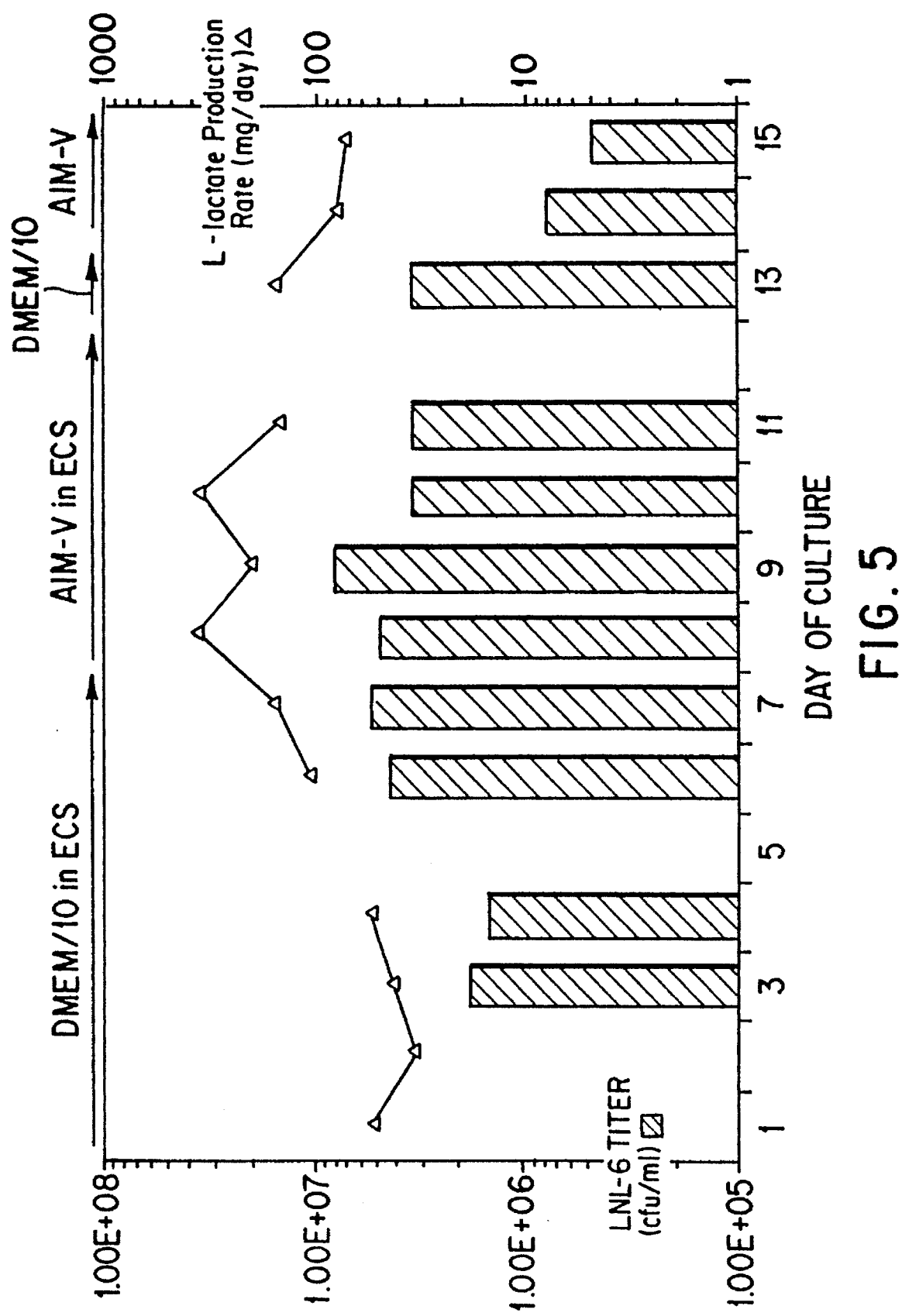

FIG. 5 shows graphically (bar graph) LNL-6 infectivity liters achived (as assessed by a colony forming assay) when LNL6-packaging cells were cultured in an ACS cartridge (B8) at 37° C. in both serum-containing and serum-free medium. Also shown is the L-lactate production during culture (connected triangles).

DETAILED DESCRIPTION OF THE INVENTION

The invention provides a method for the serum-free production of high tilers of packaged and infectious viral vectors. The method involves inoculating fibroblastic packaging cells capable of producing packaged and infectious viral vectors into an artificial capillary system (ACS) cartridge, perfusing the ACS cartridge with culture medium capable of supporting growth of the fibroblastic packaging cells, and culturing the fibroblastic packaging cells in the ACS cartridge to achieve production of packaged and infectious viral vectors, wherein the culturing occurs in the absence of serum.

Previously reported attempts to grow fibroblastic cells in vitro in the absence of serum have generally been unsuccessful. However, Pironin et al., *Int. J. Cancer* 51:980–988 (1992) reported that transforming fibroblastic cells with a ras oncogene permits growth in vitro in the absence of serum. Apparently, the presence of the oncogene causes expression of autocrine growth factors which support growth of the cells in the absence of serum. However, for obvious reasons, the use of fibroblastic cells containing a ras oncogene to produce high titers of recombinant viral vectors for use in human therapeutics would not be an attractive option.

Other attempts to bypass the necessity of serum in the in vitro culture medium have not been particularly successful. Barnes et al., *Analytical Biochemistry* 102:255–270 (1980), reportedly achieved in vitro growth of BALB 3T3 cells and Swiss 3T3 cells in serum-free medium but only if the medium was supplemented with insulin, transferrin, epidermal growth factor, fibroblast growth factor, and partially purified Gimmel factor and if the culture plates were coated with serum-containing culture medium. Furthermore, Barnes et al. reported that growth rates in serum-free medium were not as good as growth rates in serum-supplemented medium.

In contrast to the previous studies, the present invention provides a method for growing fibroblastic packaging cells in vitro in the absence of serum and without the need of supplemental exogenous growth factors or serum-coated culturing surfaces. Moreover, by the method of the present invention, it is possible to achieve serum-free production of high titers of viral vectors from fibroblastic packaging cells grown in an ACS cartridge. The ability to produce high titers of packaged and infectious viral vectors permits the transduction of target cells. Where the vectors are produced in serum-containing medium, the serum proteins may adhere to the target cell surface during transduction. In a recent study of lymphocyte transplantation, the investigators reported that recipient patients experienced Type III hypersensitivity reactions due to bovine serum proteins adherent to the infused cells. Thus, the method of the present invention reduces the chance of Type III hypersensitivity reactions due to adherent serum proteins. By the invention, transduction occurs by contacting target cells with high titers of packaged and infectious viral vectors produced in serum-free medium from the fibroblastic packaging cells cultured in an ACS cartridge. Since serum-free medium is used, there are no foreign serum proteins that adhere to the target cell surface during transduction. Thus, transduced target cells can be infused into a patient without eliciting an adverse immune response to foreign serum proteins.

Definitions

As used herein, genetic therapy involves the transfer of heterologous DNA to the certain cells, target cells, of an individual afflicted with a disorder for which such therapy is sought. The DNA is introduced into the selected target cells in a manner such that the heterologous DNA is expressed and a product encoded thereby is produced. Alternatively, the heterologous DNA may in some manner mediate expression of DNA that encodes the therapeutic product, it may encode a product, such as a peptide or RNA that in some manner mediates, directly or indirectly, expression of a therapeutic product. Genetic therapy may also be used to introduce therapeutic compounds, such as TNF, that are not normally produced in the host or that are not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, heterologous DNA is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As used herein, a therapeutically effective product is a product that is encoded by heterologous DNA that, upon introduction of the DNA into a host, a product is expressed that effectively ameliorates or eliminates the symptoms, manifestations of an inherited or acquired disease or that cures said disease.

Typically, DNA encoding the desired heterologous DNA is cloned into a plasmid vector and introduced by routine methods, such as calcium-phosphate mediated DNA uptake (*Somat. Cell. Mol. Genet.* 7:603–616 (1981)) or micro injection, into producer cells, such as packaging cells. After amplification in producer cells, the vectors that contain the heterologous DNA are introduced into selected target cells.

As used herein, operative linkage of heterologous DNA regulatory and effect or sequences of nucleotides, such as promoters, enhancers, transcriptional and translational stop sites, and other signal sequences refers to the relationship between such DNA and such sequences of nucleotides. For example, operative linkage of heterologous DNA to a promoter means that the DNA and the promoter are spatially related such that the transcription of such DNA is initiated from such promoter by an RNA polymerase that specifically recognizes, hinds to the promoter and transcribes such DNA. Heterologous DNA may be introduced into a cell by any method known to those of skill in the art.

As used herein, a target cell is a cell into which heterologous DNA is introduced for expression in the host who is being treated. Such heterologous DNA may encode a gene product, such as an enzyme, that certain individuals do not express or express in a form that is defective. Suitable target cells are known to those of skill in the art and include, but are not limited, to fibroblasts (St. Louis et al., *Proc. Natl. Acad. Sci.* 85:3150–54 (1988)) and immune cells (Keller et al., *Nature* 318:149–154 (1985) and Miller et al., *J. Virol.* 62:4337–4345 (1988)). Target cells may be removed from the individual who is being treated and modified by introducing the heterologous DNA in vitro. For example, target cells, such as lymphocytes may be transduced with retroviral vectors that have been produced by producer cells. Alternatively, it may be possible to modify target cells, such as endothelial cells that line the lungs, in vivo.

As used herein, transduced target cells refers to the portion of target cells that, after contacting target cells with a recombinant vector that includes a heterologous DNA, contain the heterologous DNA or contain the heterologous DNA and express the product encoded by the heterologous DNA. Genetically engineered target cell s, target cell s that contain heterologous DNA, are used in genetic therapy to correct genetic disorders, such as, but not limited to, certain immunodeficiency diseases, β-thalassemia, Gaucher's disease, hemophilia and cystic fibrosis, by introducing them into an individual who has an inherited or acquired genetic defect. In addition, target cells may be genetically engineered to also express DNA encoding drug resistance, such as methotrexate resistance, or drug sensitivity, such that, when such DNA is expressed, the cells may be selectively expanded or destroyed in vivo and to express therapeutically effective substances, including antibodies and tumor necrosis factor.

As used herein, transduction is the process whereby a viral vector specifically binds to cell surface receptors and enters the cell. It is a process akin to viral infection, except that viral vectors are modified viruses and, upon introduction, into a target cell, generally, do not cause productive infection. For example, retroviral vectors are generally designed to be replication-incompetent.

As used herein, the concentration of transduced target cells refers to the number of transduced target cells/total number of target cells contacted with the vector. The concentration may be expressed as a percentage (number of transduced target cells/total number of target cells×100).

As used herein, a recombinant vital vector is a vector that includes DNA that is derived from an RNA or DNA virus and also includes heterologous DNA, which is generally in operative linkage with a promoter and other transcriptional and translational regulatory sequences or signals that are recognized by the host cell in which the virus from which such vector is derived can replicate. Recombinant vectors may be either retained as part of independently replicating episomal elements or integrated into the genome of the host cell.

Recombinant viral vectors useful for genetic therapy are typically derived from viruses that infect and replicate in eukaryotic cells and thereby serve as a means for introducing heterologous DNA into eukaryotic cells. Recombinant viral vectors that remain episomal include an origin of replication, whereby DNA synthesis can be initiated. Recombinant vectors that integrate into the genome must include DNA sequences necessary to effect integration. Preferred recombinant viral vectors used for genetic therapy are generally selected from among those which integrate into the host cell genome.

As used herein, a producer cell is cell in which recombinant viruses can replicate and can thereby be amplified. Some producer cells also package and secrete recombinant viruses into the medium in which the cells are cultured. The recombinant viral vectors produced by producer cells are used to transduce target cells. Producer cells are typically immortalized or transformed cell lines that are cultured in vitro and are designed to produce maximal amounts of recombinant vectors. For example, retrovirus packaging cell lines are producer cells that include trans-acting factors necessary to package defective retroviral vectors.

As used herein, adoptive immunotherapy is a therapeutic method, whereby cells of the immune system are removed from an individual, cultured and/or manipulated in vitro, and introduced into the same or a different individual as part of a therapeutic treatment for an acquired or inherited disease. Immune cells and adoptive immunotherapeutic methods may be adapted for use in methods of genetic therapy as vehicles for delivery of heterologous DNA.

As used herein, immune cells include any cells that participate the functioning of the immune system. Lymphoid cells include lymphocytes, macrophages, and monocytes that are derived from any tissue in which such cells are present. In general lymphoid cells are removed from an individual who is to be treated.

As used herein, a growth promoting substance is a substance, that may be soluble or insoluble, that in some manner participates in, induces cells or otherwise activates cells, directly or indirectly, to differentiate or proliferate. Growth promoting substances include mitogens and cytokines, including interleukins, colony stimulating factors, and any other of such factors that are known to those of skill in the art. For example, many types of cells, including target cells, such as lymphocytes, which in vitro require IL-2, have absolute requirements for certain growth promoting substances. Growth promoting substances are well known to those of skill in the art. Many such substances, such as the interleukins 1–7, have been cloned and expressed in vitro. It is within the level of skill in the art, to select appropriate growth factors in order for culturing both producer cells and target cells in a bioreactor. Other substances, including polycations, such as protamine, may be added to the bioreactor in order to promote viral infectivity by, for example, enhancing viral adsorption to the target cell surface.

As used herein, a therapeutically effective amount of transduced target cells is a sufficient concentration and number of transduced target cells for at least single infusion of such cells into an individual for genetic therapy. Upon infusion of a therapeutically effective amount of transduced target cells, a sufficient amount of a product produced by the transduced cells is expressed to ameliorate or eliminate the symptoms or manifestations of an inherited or acquired disease. In order to effect a cure or a substantial reduction of the symptoms or manifestations of the disease, it may be necessary to repeat perform multiple infusions and/or to periodically repeat such infusions.

As used herein, an artificial capillary system (ACS) consists of a hollow capillary system bioreactor and means for pumping and collecting perfusing medium. An ACS is a hollow shell that encases a plurality of semi-permeable capillaries through which medium is perfused.

As used herein, the extra capillary space (ECS) is the space in which the cells grow that is external to the semi-permeable capillaries and bounded without by the shell of the ACS. The ECS is alternatively referred to as the extra fiber space (EFS).

As used herein, the ECS cell medium is the medium in which the cells in the ECS are growing. It may also be referred to as the ECS supernatant. It contains secreted cellular products, including secreted vital particles, diffusible nutrients and any other compounds, including growth promoting or suppressing substances, such as lymphokines and cytokines, that have been added to the ECS medium, or diffusible products that have been added to the perfusing tissue culture medium. The particular components included in the ECS is a function not only of what is inoculated therein, but also of the characteristics of the selected hollow capillary.

Thus, as used herein, an ACS cartridge consists of an outer shell casing that is suitable for the growth of mammalian cells, a plurality of semi-permeable hollow capillaries encased within the shell that are suitable for the growth of mammalian cells on or near them, and the ECS, which contains the cells and the ECS cell supernatant.

The present invention preferably involves the serum-free culture of fibroblastic packaging cells in an ACS cartridge. By "serum-free" is intended culturing the packaging cells in the absence of mammalian serum. Serum is the fluid which separates from blood on coagulation. Examples of mammalian serum include fetal bovine serum, newborn bovine calf serum, bovine calf serum, horse serum, human serum, chicken serum, fetal pig serum, goat serum, guinea pig serum, lamb serum, porcine serum, rabbit serum, rat serum, and mice serum.

Bovine serum, and in particular, fetal bovine serum, are commonly used to support the in vitro culture of numerous cell types. This is especially true for the in vitro culture of mouse fibroblastic cells (e.g., NIH 3T3 cells). As discussed above, the present invention obviates the need for the serum supplement. Thus, the invention is directed to culturing fibroblastic packaging cells without the presence of bovine serum. More particularly, the cells can be cultured in the absence of the almost universally used fetal bovine serum.

As used herein, culture medium includes any culture medium that is suitable for the growth or maintenance of mammalian fibroblastic cells in vitro. Examples of such medium include, but are not limited to AIM-V, Dulbecco's minimal essential tissue culture medium (DMEM, Gibco, Grand Island, N.Y.), RPMI, and Iscove's medium (GIBCO, Grand Island, N.Y.).

As used herein, complete tissue culture medium (cTCM) consists of the proprietary formula AIM-V (GIBCO, Grand Island, N.Y.) and also contains 10 μg gentamicin/ml (GIBCO), 50 μg streptomycin/ml (GIBCO), 50 μg penicillin/ml (GIBCO), 1.25 μg fungizone/ml (Flow Laboratories, MacLean, Va.).

These tissue culture media are well known and are available to the skilled artisan. Other suitable tissue culture media are also and readily available.

Artificial Capillary Systems

Artificial Capillary Systems (ACS) are known in the art (Knazek et al., U.S. Pat. Nos. 4,220,725, 4,206,015, 4,200, 689, 3,883,393, 3,821,087, WO 90/02171). An ACS includes the bioreactor, pumping means for perfusing medium through the system, reservoir means for providing and collecting medium, and other components, including electronic controlling, recording and sensing devices.

A typical ACS, such as the CELLMAX™ 100 ACS (Cellco Advanced Bioreactors, Inc., Kensington, Md.), which is described in PCT International Application WO 90/02171, consists of a standard glass media bottle, which serves as the reservoir, a stainless steel/Ryton gear pump, the autoclavable bioreactor, which includes the capillaries and shell casing in which cells are cultured, and medical grade silicone rubber tubing, or other connecting means, which serves as a gas exchanger to maintain the appropriate pH and $PO_2$ of the culture medium. All components are secured to a stainless steel tray of sufficiently small dimensions to enable four such systems to fit within a standard tissue culture incubator chamber. The pump speed and automatic reversal of flow direction are determined by an electronic control unit which is placed outside of the incubator and is connected to the pump motor via a flat ribbon cable which passes through the gasket of the incubator door. The pump motor is magnetically coupled to the pump and is lifted from the system prior to steam autoclaving. Tissue culture medium is drawn from the reservoir, pumped through the lumina of the hollow fibers, and then passed through the gas exchange tubing in which it is re-oxygenated and its pH readjusted prior to returning to the reservoir for subsequent recirculation.

The ACS cartridge contains a multitude of semi-permeable tube-shaped capillaries encased within a hollow shell. ACS cartridges have been used to cultivate viruses, including herpes simplex virus, hepatitis virus, equine encephalitis virus, mouse mammary tumor virus and human immunodeficiency virus (Meyers et al., U.S. Pat. No. 4,546,083; Markus et al., U.S. Pat. No. 4,301,249; Johnson et al., *Appl. Envir.* 35:431 (1978); and Tsang et al. publication of Poster presentation at Bio-Expo, 1986, Boston Mass.)

ACS cartridges, contain a multitude of tube shaped semi-permeable capillaries encased in a hollow shell. Cultured cells grow and fill the spaces between the capillaries and are fed by passage of nutrients through the capillary walls from medium that is perfused through the lumina of the capillaries. Preferred ACS cartridges for use in the invention are the B3, B4, and B8 cartridges (Cellco Advanced Bioreactors, Inc., Kensington, MD) PCT International Application WO 90/02171 contains a complete description of the B3 and B4 cartridges.

The B3 bioreactor cartridge contains several thousand tube-shaped, semi-permeable membranes, which provide about a 1.1 $m^2$ surface area. The B4 bioreactor cartridge is somewhat larger than the B3 cartridge and provides a capillary surface area of about 1.6 $m^2$. The B8 cartridge provides a capillary surface area of only about 0.1 $m^2$. The capillaries, which are each approximately 250 μm in diameter, are pulled through a polycarbonate tube that is about 12 inches in length, and the extra-capillary volume is filled at each end with a polymeric material in a manner such that liquid can flow through the lumina of the capillaries to exit at the opposite end of the shell. The capillary walls nominally restrict passage to substances having molecular weights less than a desired cut-off range. The selected capillary should be semi-permeable to permit the passage of nutrients into the ECS and should be of a material, such as DEAE-cellulose or polypropylene, on which or in the vicinity of which the mammalian cells are able to grow. For example, the capillaries used in the B3, B4, and B8 cartridges are cellulosic or polypropylene capillaries fibers whose walls nominally restrict diffusion to substances having molecular weights in the range of 3000 to 4000 Daltons. This molecular weight cut-off range is suitable for use in practicing this invention because it is sufficiently small to prevent diffusion of packaged recombinant viral vectors out of the ECS. The capillaries divide the cartridge into the ECS, which is also referred to as the extra-fiber or shell-side space, within which minimal bulk flow of perfusion medium occurs by ultrafiltration through the capillary wall. The ECS volume of the B3 cartridge is about 50 ml and that of the B4 cartridge is about 100 ml. The B8 cartridge has an ECS volume of only 7 ml.

The particular cartridge selected for use depends upon various parameters, including the requirements of the cells that are being cultivated, the materials perfusing through the lumina of the capillaries, and the cellular products and recombinant vectors that are being harvested. It is within the level of skill in the art to select an appropriate cartridge. In the present invention, capillaries will generally be selected such that they are impermeable to the packaged vital vectors in order to maximize the concentration thereof in the ECS and to prevent undesirable contamination of the perfusing medium with such virions.

Tissue culture medium perfuses through the lumina of the capillaries and is also included within the ECS surrounding said fibers. The tissue culture medium, which may differ in these two compartments, is capable of supporting cell growth and proliferation. Tissue culture medium, which is generally oxygenated, is provided in a reservoir from which it is pumped through the fibers. The flow rate can be controlled by the varying the pump speed. In addition, the direction of flow of the perfusing medium can be reversed (PCT International Application WO 90/02171).

The ECS and/or the perfusing medium may additionally contain an effective amount of at least one growth promoting or suppressing substance, such as IL-2, that specifically promotes the expansion or suppression of the cultured cells, particularly the selected target cells, such as lymphocytes, in which the effective amount is an amount sufficient for the cells to be maintained or proliferate in vitro. The ECS and/or perfusing medium are supplemented with additional ingredients including serum, serum proteins, and selective agents for selecting genetically engineered or modified cells. The selected method is a function of, among other variables, the type of cells, their intended use, and the extent to which they adhere to the capillaries. However, as discussed above, the growth of fibroblastic packaging cells can be supported by DMEM and AIM-V without the necessity of serum or exogenous growth promoting substances such as cytokines.

The flow rate can be increased as the number of cells increases with time. Typically the initial flow rate of the medium is adjusted to about 30 to 40 ml/min and is then increased up to about 300 ml/min as the number of cells increases with time. The direction of perfusion of the medium through the lumina of the capillaries may be periodically and automatically reversed, typically every ten minutes, in order to provide a more uniform distribution of nutrient supply, waste dilution, and cells within the space surrounding the capillaries.

The entire system is sterilized prior to cell inoculation and is designed for operation in a standard air-$CO_2$ tissue culture incubator. Upon inoculation, the cells settle onto the surface of the capillaries, through which nutrients pass to feed the cells and through which metabolic waste products pass to be diluted into the large volume of the recirculating perfusate. A suspension of cells is inoculated into the extra-capillary space (EFS) usually through one of two side ports. The lumina are perfused with cell culture medium and the cells are maintained in vitro for the desired period of time. As the cells are cultured, the perfusing medium can be periodically monitored for L-lactate production or glucose consumption. The perfusing medium is replenished by replacing the medium in the reservoir bottles whenever glucose concentration drops to about 30 to 40% of its initial value.

After culturing the cells, the ECS and/or the cells may be harvested. In accordance with this invention, the ECS that contains packaging cells is harvested and used to transduce target cells that are cultured in a second bioreactor. After transduction, which may be repeated multiple times, and incubation, the target cells are harvested. Any suitable means know to those of skill in the art may be used to harvest the ECS and to harvest the target cells. For example, in order to harvest the ECS, the bioreactor cartridge is removed from the incubator and placed in a laminar flow hood. The bioreactor cartridge containing the target cells is given a single gentle shake, which usually suspends about 30–40% of cells, and the contents of the ECS, including the loosened cells, are drained into a side port bottle. Fresh medium is added to the ECS and incubation of the target cells can be continued.

Packaged vector production continues at high rate as long as the ECS is periodically harvested and replaced with fresh medium. Other methods known to those of skill in the art for removing the ECS and cultured cells from the bioreactor may be used.

Selection of the recombinant viral vector and production of high titers thereof

The preparation and selection of the recombinant viral vector DNA encoding at least one gene product is within the level of skill in the art. In general, the selected recombinant viral vector is one that can be replicated and packaged by selected producer cells but not by the selected target cells. It may be a vector that is integrated into a host cell genome, such as an SV40-derived or retrovirus-derived vector, or one, such as a vector derived from Epstein Barr virus, which includes an origin of replication, that remains episomal.

The gene product may be a therapeutic product, such as an anti-cancer or anti-viral agent; it may be a product, such as adenosine deaminase or immunoglobulin, that the recipient either fails to produce or produces in a mutated defective form because of a genetic defect; it may be a marker, such as DNA that encodes neomycin or methotrexate resistance, whereby the reinfused target cells may be selected or detected; or it may encode a product that regulates expression of another gene product. Selection, cloning and insertion of the heterologous DNA into the recombinant viral vector is within the level of skill in the art and may be effected by any of the well known methodologies therefor.

Any recombinant viral vector derived from viruses that can replicate in eukaryotic cells may be used. The selected heterologous DNA is inserted into the recombinant viral vectors, which is then introduced into packaging cells by any means known to those of the skill in the art. The transfected producer cells are then cultured in an ACS cartridge for sufficient amount of time to produce high titers of packaged and infectious recombinant viral vectors. What constitutes a "sufficient amount of time" can easily be determined from the Examples provided herein.

Preferred embodiments employ recombinant retroviral vectors produced by a packaging cell line that secretes packaged replication incompetent infectious retroviral particles into the ECS of an ACS cartridge. Preferred retroviral vectors are those that are suitable for genetic therapy. Suitability for use in genetic therapy necessitates minimizing the possibility for recombination to produce replication competent retrovirus or to activate cellular oncogenes and the retroviral vector must be packaged in packaging cell lines that do not concomitantly produce helper virus. Such retroviral vectors may be constructed by means known to those of skill in the art may be retroviral vectors known to those of skill in the art or may be derived therefrom.

Typically, suitable retroviral vectors include: the LTRs; necessary regulatory signals and retroviral sequences to produce and integrate proviral DNA into the host cell genome; and heterologous DNA, which includes DNA that encodes a detectable marker and/or selectable marker. The heterologous DNA is inserted in place of all or portions of the retroviral structural genes in operative linkage with transcriptional and translational regulatory sequences including a promoter, such as the 5' LTR or endogenous promoter, that is recognized by an RNA polymerase in the target cell.

Retroviral vectors are generally constructed by preparing cDNA, which is inserted into a convenient plasmid, such as pBR322. Desired insertions and deletions are effected using standard methods, and the plasmids are introduced into selected packaging cell lines in order to generate retroviral particles. Introduction of the plasmids into the packaging cell line may be effected by any method known to those of skill in the art. For example, the DNA may be transfected by Ca-phosphate mediated transfection (PCT International Application WO 90/01870), DEAE-dextran mediated transfection methods, lysozyme fusion, direct uptake or any other method known to those of skill in the art. Typically the plasmids are first introduced into an ecotropic cell line to produce infectious packaged particles, which are then transduced into an amphotropic packaging cell line, and cultured in selective medium, and cellular clones are selected. The selected clones are tested for the ability to produce packaged retroviral vectors without concomitant helper virus production. Those that do not produce helper virus and/or replication competent packaged retroviral vectors are suitable for use in producing packaged viruses for transducing target cells used in genetic therapy. Examples of retroviral vectors from which clinically useful recombinant retroviral vectors that can be modified by insertion of heterologous include, but are not limited to, the retroviral constructs: pN2 (Keller et al., *Nature* 318:149–154 (1985); and U.S. Pat. No. 4,861, 719 to Miller); pLHL, which is derived from N2 (Miller et al., *Cold Spring Harbor Symp. on Quantitative Biology*, Vol. LI, Cold Spring Harbor Laboratory (1986), pp. 1013–1019); pSDHT (Miller et al., *Somat. Cell. Mol. Genet.* 12:175–183 (1986)), which includes the bacterial marker gene that encodes the neomycin resistance gene (Neo$^R$); pLPL (*Proc. Nat'l Acad. Sci. USA* 80:4709–4713), which includes the gene encoding the selective marker hypoxanthine-guanine phosphoribosyltransferase, HGPRT; and LNL-6 (Bender et al., *J. Virol.* 61:1639 (1987)), which also contains the Neomycin-resistance gene (Neo$^R$) used in gene marking studies.

Derivatives of these vectors, such as those that include the heterologous gene or genes of interest, may be constructed by inserting selected heterologous DNA into a retroviral vector in operative linkage with a promoter, which recognized by a target cell RNA polymerase, and other transcriptional and translational regulatory signals. For example, retroviral vectors SSC and SSCX, ATCC Accession Nos. 67760 and 67761, respectively, which are derived from N2, encode a soluble form of the glycoprotein receptor CD4, which as been proposed for use in AIDS therapy. SSC and SSCX have been packaged using the PA317 cell line (ATCC Accession No. CRL 9078). The construct pLPL2 (U.S. Pat. No. 4,861,719 to Miller), which is derived from pLPL by including additional deletions, such as deletion of the second packaging signal in the 3' LTR, which prevents packaging of pBR322 DNA.

In a preferred embodiment, the retroviral vector LASN (see Hock et al., *Blood* 74:876–881 (1989)), which is a derivative pLNL6, an N2 derivative (Bender et al., *J. Virol.* 61:1639 (1987)), and which encodes ADA, is produced in high titer in an ACS cartridge by a packaging cell line derived from PA317 (ATCC Accession No. CRL 9078). The LASN plasmid vector includes DNA that encodes 5' LTR, the psi$^+$ packaging signal, which includes gag protein encoding sequences, but which have been modified by changing ATG to TAG to prevent translation of any gag encoding sequences (Bender et al., *J. Virol.* 61:1639 (1987)); the cDNA encoding the ADA gene inoperative linkage with the 5' LTR; the neo gene in operative linkage with the SV40 early region promoter and enhancers; and the 3' LTR, which includes a polyadenylation site. The AUG start cod on for ADA mRNA begins in the LTR, continues through ADA sequences, the SV40 sequences and neo sequences and terminates in the 3' LTR. The LASN plasmid vector has been transfected into the packaging line, PA317 (ATCC Accession No. CRL 9078), which produces packaged LASN retroviral particles that have an amphotropic host range (Hock et al., *Blood* 74:876–881 (1989)) but which does not produce detectable helper virus.

The LASN-producing or LNL-6 producing PA317 cell line is inoculated into the ECS of an ACS cartridge and cultured under conditions whereby packaged LASN retroviral particles or LNL-6 retroviral particles are produced in the ECS medium high tiler. As shown in the Examples herein, production of packaged and infectious LASN and LNL-6 virions can occur in either serum-containing or serum-free culture medium. Preferably, however, the recombinant retroviral vectors are packaged to high liters in the ECS in serum-free medium as shown in Example 6.

Preparation of producer cells

Recombinant viral vectors used for genetic therapy must be able to infect target cells, but should not harm the host. Therefore, the viruses from which they are derived should be modified such that they do not commandeer target cell biochemical pathways to the detriment of the target cell and/or host into which the target cells are introduced. Consequently, in order to amplify recombinant viral vectors that contain heterologous DNA of interest, the recombinant vectors must be cultured in vitro in packaging cells in which they can be replicated.

In preferred embodiments, recombinant vital vectors are amplified in packaging cells lines that are cultured in an ACS cartridge and secrete the recombinant vectors into the ECS in a form in which the recombinant vectors can be introduced into target cells. In particular, packaging cell lines that produce packaged and infectious, replication-incompetent, recombinant retroviral vectors that contain heterologous DNA are cultured in an ACS cartridge until high titers of packaged retroviral vector particles accumulate in the ECS.

Suitable packaging cells lines can be derived from fibroblastic cells. Fibroblastic cells can be obtained according to conventional techniques from connective tissue of mammals including mice, rats, guinea pigs, rabbits, cows, horses, pigs, and humans. Preferably, the packaging cell line is derived from murine fibroblastic cells. More preferably, the packaging cell line is derived from mouse fibroblastic cells. Still more preferably, the packaging cell line is derived from mouse 3T3 fibroblastic cells. Most preferably, the packaging cell line is derived from PA317.

Numerous mouse fibroblastic cells are available which are suitable for constructing a packaging cell line. The include NIH/3T3 cells (ATCC CRL 1658; which are described in *J. Virol.* 4:549 (1969) and *Cell* 16:63 (1979)); 3 T3-Swiss albino cells (ATCC CCL 92; which are described in *Proc. Natl. Acad. Sci.* USA 51:66 (1964)); 3T6-Swiss albino cells (ATCC CCL 96; which are described in *J. Cell Biol* 17:299 (1963)); and BALB/3T12-3 cells (AFCC CCL 164; which are described in *J. Cell Physiol* 72:141 (1968)).

Packaging cell lines can be constructed from one or more of these mouse fibroblastic cell lines according to the methods described in U.S. Pat. No. 4,861,719 to Miller; Miller et al., *Biotechniques* 7:980 (1989); Miller et al., *Molecular and Cellular Biology* 6:2895 (1986); Mann et al., *Cell* 33:153–159 (1983); and Hock et al., Blood 74:876–881 (1989).

Known packaging cell lines include psi$^2$ (Mann et at., *Cell* 33:153–159 (1983)); NIH 3T3 TK (Miller et al., *Mol. Cell. Biol.* 6:2895–2902 (1986)); PA317 (ATCC Accession No. CRL 9078) (U.S. Pat. No. 4,861,719); and PE501, which is similar to PA317, but produces packaged retroviral particles that have an ecotropic host range (Hock et al., *Blood* 74:876–881 (1989)).

A packaging cell line, such as PA317, can transmit packaged viral RNAs, including those that encode heterologous DNA, as long as the viral RNA includes the proper cis-acting elements, such as the packaging signal. The packaged viral particles that are produced by PA317 are amphotropic, and, thus, can infect a broad range of mammalian target cells.

In a preferred embodiment, the retroviral vector LASN or LNL-6 is produced by a packaging cell line that has been derived from PA317.

Culturing producer cells in an ACS cartridge

Prior to use, an ACS, such as the CellMAX™ 100, is steam autoclaved, continuously perfused with recirculating deionized water, drained, flushed, and perfused with the selected tissue culture medium in both the ECS and perfusate pathways. All operations are performed in sterile conditions, such as in a sterile laminar flow hood.

A sufficient amount, generally about $10^5$–$2\times10^6$ packaging cells/ml, of cells in a sufficient volume to fill the ECS of a bioreactor cartridge is inoculated into the pre-sterilized cartridge, such as a B3, B4, or B8 bioreactor cartridge (Cellco Advanced Bioreactors, Inc., Kensington, Md.). The inoculated bioreactor is transferred to a standard incubator, perfused with medium at an appropriate temperature, generally about 32° C. to about 37° C. and maintained under these conditions.

After the cells settle, culture medium is continuously perfused through the HF bioreactor by means of externally applied pressure, such as a pump. A reservoir that contains tissue culture medium, the HF bioreactor cartridge, and pumping means are connected by tubing, typically silicone rubber, which also serves as an oxygenator. The medium may be oxygenated by any means known to those of skill in the art. The silicone rubber tubing simultaneously serves as a membrane gas exchanger to replenish oxygen and, if the medium is buffered with bicarbonate, to maintain the pH via $CO_2$ transport into the perfusion medium. Medium that is buffered with systems other than bicarbonate do not necessarily require $CO_2$ in the incubator.

Perfusion is continued for a sufficient time and under conditions, whereby the vector is released into the ECS, which then contains high titers of the recombinant vector. The conditions, which include, the tissue culture medium, incubation temperature and incubation time, are chosen as a function of the requirements of the producer cells and recombinant viral vector. Determination and optimization of such conditions are within the level of skill in the art.

During the incubation period, the reservoir containing the perfusing medium is replaced in order to maintain a sufficiently high concentration of glucose and other diffusible nutrients in the ECS and for waste removal.

Typically, the perfusate is replenished several times a week by replacing the reservoir bottle with one containing fresh medium. Incubation continues for at least about one to thirty days or more days. During the incubation period, the ECS is periodically harvested and contacted with target cells. After the cells have been incubating for one to several days to a week or so, the ECS can be harvested. The ECS can be harvested batch wise, periodically, or continuously or by any variation thereof known to those of skill in the art. It may also be connected to the ECS of a second bioreactor that contains target cells, as shown, for example, in FIG. 3.

In preferred embodiments, LASN-producing or LNL-6 producing PA317 cells, which are suspended in either serum-containing or serum-free tissue culture medium, are inoculated into a B3, B4, or B8 bioreactor, (Cellco Advanced Bioreactors, Kensington, Md.) via the side ports. The bioreactor is attached to a perfusion circuit, the cells are permitted to settle onto the fibers for about 15 minutes to several hours before perfusion is initiated. After perfusing overnight or for day or two the ECS can be harvested, batch wise or by directly introducing it into a second bioreactor using a dual perfusion circuit, fresh ECS medium is added and perfusion continues. If the ECS is harvested periodically, about once a day, the LASN-producing and LNL-6 producing cells continue to produce high titers, at least about $10^5$ cfu/ml, for up to at least 6 to 7 weeks.

Viral liter may be measured by any method known to those of skill in the art (U.S. Pat. No. 4,861,719 to Miller; and U.S. Pat. No. 4,868,116 to Morgan et al.) Typically viral tiler is measured as colony forming units/ml (cfu/ml).

Selecting target cells and transducing them with recombinant viral vectors produced by cells cultured in an ACS cartridge Target cells, such as fibroblasts (Palmer et al., *Proc. Natl. Acad. Sci.* 84:1055 (1987); St. Louis et al., *Proc. Natl. Acad. Sci.* 85:3150–54 (1988) and PCT International Application WO 90/01870) epithelial cells (see, U.S. Pat. No. 4,868,116 to Morgan et al.) and immune cells, such as lymphocytes, are obtained either from the patient, who has the inherited or acquired disease or from another donor. The selected target cells are contacted with the harvested recombinant viral vectors that were produced in an ACS cartridge to produce transduced target cells. In order to enhance infectivity of the viral vector, polycations, such as protamine at concentrations of about 5–10 µg/ml, may be added to the harvested viral vectors or to the bioreactor in which the producer cells are cultured. Contacting may be effected by any method known to those of skill in the art. The target cells are then inoculated into the ECS of a second bioreactor, which has been autoclaved and prepared as described above for the producer cells, and incubated as described above.

The target cells may be transduced, either before or after inoculation into the ECS of the second bioreactor, by contacting with the ECS medium from a first bioreactor that contains producer cells. The target cells may be mixed with harvested ECS medium, may be introduced into a second bioreactor into which the harvested ECS medium is inoculated or the ECS of the second bioreactor may be connected to the ECS of a first bioreactor that contains producer cells and is continuously or intermittently inoculated. The target cells are contacted with harvested vector-containing ECS medium one or more times.

Target cells can be harvested by gently shaking the bioreactor and pouring the suspended cells into a side port bottle. Generally about $10^{10}$ target cells are used for one treatment and, ideally, 100% should be transduced.

In preferred embodiments, lymphocytes are inoculated into a second bioreactor and then transduced with the ECS serum-free medium from a first bioreactor, which contains packaged infectious replication-incompetent retroviral vectors. Preferably, all cultures (i.e., packaging cell culture and target cell culture) occur in serum-free medium.

Figure 3:
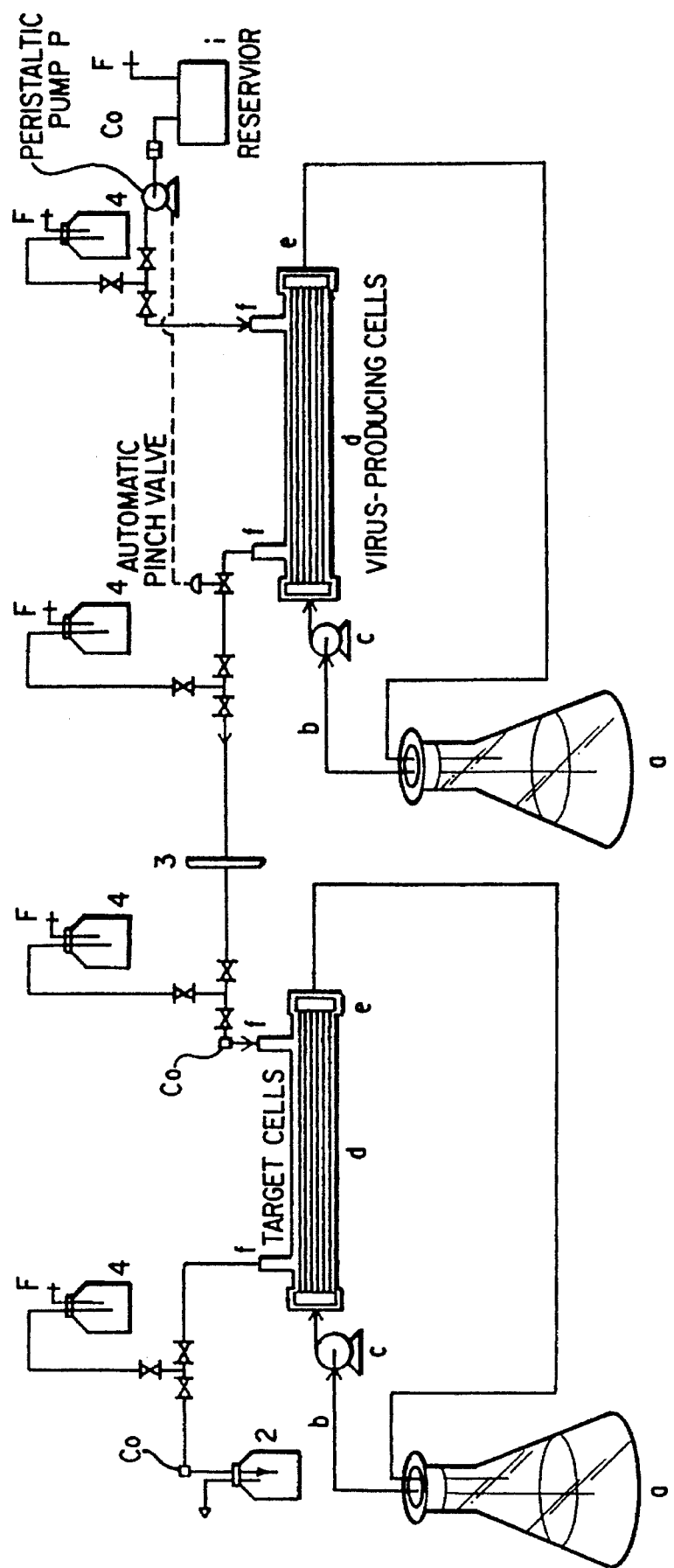
FIG. 3 presents a schematic diagram of a dual perfusion circuit for direct and continuous inoculation of the ECS from a hollow fiber bioreactor that contains a viral packaging or producing cell line into the ECS of a hollow fiber bioreactor that contains target cells. The perfusion circuit includes: reservoirs (a), connecting tubing (b), media pumps (c), and hollow fiber bioreactors (d). Cells are injected into the ECS through the loading side-ports (f).

In a preferred embodiment, transduction is effected continuously or intermittently using a dual perfusion circuit as shown in FIG. 3, discussed below, by connecting the ECS of the second bioreactor to ECS of a first bioreactor in which retroviral vector-producing cells have been inoculated. The target cells are then repeatedly exposed to ECS serum-free medium from the first bioreactor. A high percentage of target cells can thereby be transduced.

The dual bioreactor perfusion circuit

Continuous or intermittent inoculation of target cells with recombinant retroviral vectors may be effected by directly pumping the ECS from the first bioreactor that contains the producer cells into the ECS of the second bioreactor that has been inoculated with target cells. This may be accomplished using the dual perfusion circuit, pictured in FIG. 3. Preferably all cultures are performed in serum-free medium.

As shown in FIG. 3, the perfusion circuits of the two bioreactors are separated by a pinch clamp (represented by (|x|) in FIG. 3). A peristaltic pump, is used to introduce fresh medium into the bioreactor that contains the producer cells. When the peristaltic pump is operating, the pinch clamp opens, thereby connecting the ECS of the first bioreactor via a side port to that of the second bioreactor via a side port. ECS medium (preferably serum-free) that contains recombinant retroviral vectors is forced out of the first bioreactor through the connecting tubing and pinch clamp and into the second bioreactor. Fresh medium (preferably serum-free) is introduced through the second side port of the producer bioreactor. A filter that is designed to remove blood leukocytes, is placed in the tubing between the two bioreactors, interposed between the pinch clamp and the second bioreactor. This prevents contamination of the target cells by the packaging cells. Excess medium from the ECS of the second bioreactor is forced through the second side port into an overflow flask. The peristaltic pump may be operated continuously or periodically. In preferred embodiments, the pump is operated for about 1 minute per hour at a pressure sufficient to introduce about 10 ml of vector-containing ECS medium into the ECS of the second bioreactor that contains target cells.

The following examples are included for illustrative purposes only and are not intended to limit the scope of the invention.

EXAMPLE 1

Production of ADA-containing retroviral particles

LASN-producing cells were the gift of Dr. Dusty Miller. The construction of the LASN retroviral vector that contains the ADA gene in operative linkage with the LTR and the helper-free cell line that produces packaged LASN retroviral vector particles is described in U.S. Pat. No. 4,861,710 to Miller and in Hock et al., *Blood* 74:876–881 (1989) is discussed above. The packaging cell line and LASN vector were prepared using publicly available and well known starting materials.

Briefly, LASN is a derivative of the vector LNL6 (Bender et al., *J. Virol.* 61:1639 (1987)), which is a derivative of the well-known vector N2 (*Nature* 318:149–154); Armentano et al., *J. Virol.* 61:1639 (1987)). LASN includes, starting at the 5' LTR, which is the MoMLV LTR, the extended packaging signal, psi$^+$, ADA cDNA under control of the LTR, the SV40 early region promoter and enhancer, the bacterial neo gene under control of the SV40 promoter, the second LTR, and a polyadenylation site. ADA encoding sequences extend through the SV40 and neo and into the 3' LTR. A plasmid containing the LASN sequences was introduced into an ecotropic packaging cell line, PE501, and virus from these cells was used to infect PA317, ATCC accession no. CRL 9078, and G-418-resistant LASN-producing PA317 cells were isolated.

LASN-producing PA317 cells were grown in T-150 flasks and cultured to produce confluent monolayers. The cells from three T-150 culture flasks (about $4.5 \times 10^7$ LASN-producing PA317 cells) were trypsinized, resuspended in complete tissue culture medium (cTCM), which contains 10% heat-inactivated fetal calf serum (FCS) (Hyclone, Logan, UTAH), and centrifuged at 800×g for about 10 minutes at room temperature. The cell pellet was resuspended in 100 ml cTCM and inoculated into the ECS of a B4 ACS cartridge (Cellco Advanced Bioreactors, Kensington, Md.) via the side ports. All operations were performed in a sterile laminar flow hood.

Prior to use, the silicone rubber tubing flow path from the bioreactor culture system had been connected to the pump and reservoir and steam autoclaved with side port tubing and bottles at about 121° C. for 20 minutes.

Using sterile technique, a B4 bioreactor cartridge was removed from its package and inserted into the sterilized silicone rubber tubing pathway. The side port bottles were attached to the side ports of the B4 HF cell bioreactor. The distilled water in the EFS of the bioreactor was drained into empty side port bottles and discarded. The system was perfused with 0.8 liters of deionized water overnight at 37° C. The perfusion pathway and extra-capillary space of each system were then drained and flushed with Dulbecco's minimal essential tissue culture medium (DMEM, Gibco, Grand Island, N.Y.) which was then discarded and replaced with cTCM, which contained 45 gm glucose/liter DMEM, 10% heat-inactivated FCS, 50 units of penicillin/ml, 50 µg streptomycin/ml, and 2.5 µg amphotericin B/ml, which had been placed in the reservoir of the perfusion circuit.

The bioreactor culture system was then transferred to a standard tissue culture incubator, which was held at 37° C. and contained a humidified 5% $CO_2$ in air atmosphere. Perfusion was initiated at a rate of about 100 ml/minute.

After an overnight perfusion, the bioreactor was removed from the incubator and the ECS was inoculated with 100 ml of the resuspended LASN-producing PA317 cells via the side port bottles. The entire CELLMAX™ bioreactor unit was then placed into the incubator, but not perfused for 4 hours, in order to facilitate uniform attachment of cells to the fibers. Subsequent perfusion was commenced at a rate of about 40 ml per minute and gradually increased to about 300 ml per minute during the course of the culture in order to insure that the cells were adequately oxygenated. The direction of flow of perfusing medium was not reversed.

Glucose concentration of the perfusing medium was monitored about every 1–4 days. The perfusion medium was replaced when glucose concentration had dropped to about 30–50% of the initial value of about 4.5 gr/l. The medium replacements were performed in a laminar flow hood.

As expected, the perfusate, which was assayed for virus by a colony forming assay, contained no detectable virus. The viral particles are about 150–200 nm in diameter, which is too large to diffuse through the capillary walls.

At the indicated times (see FIGS. 1a and 1b), the medium in the ECS, which contained the viral particles, was harvested and replaced with fresh cTCM. The harvested medium was stored at $-70°$ to $-80°$ C. awaiting assay for virus content.

Figure 1:
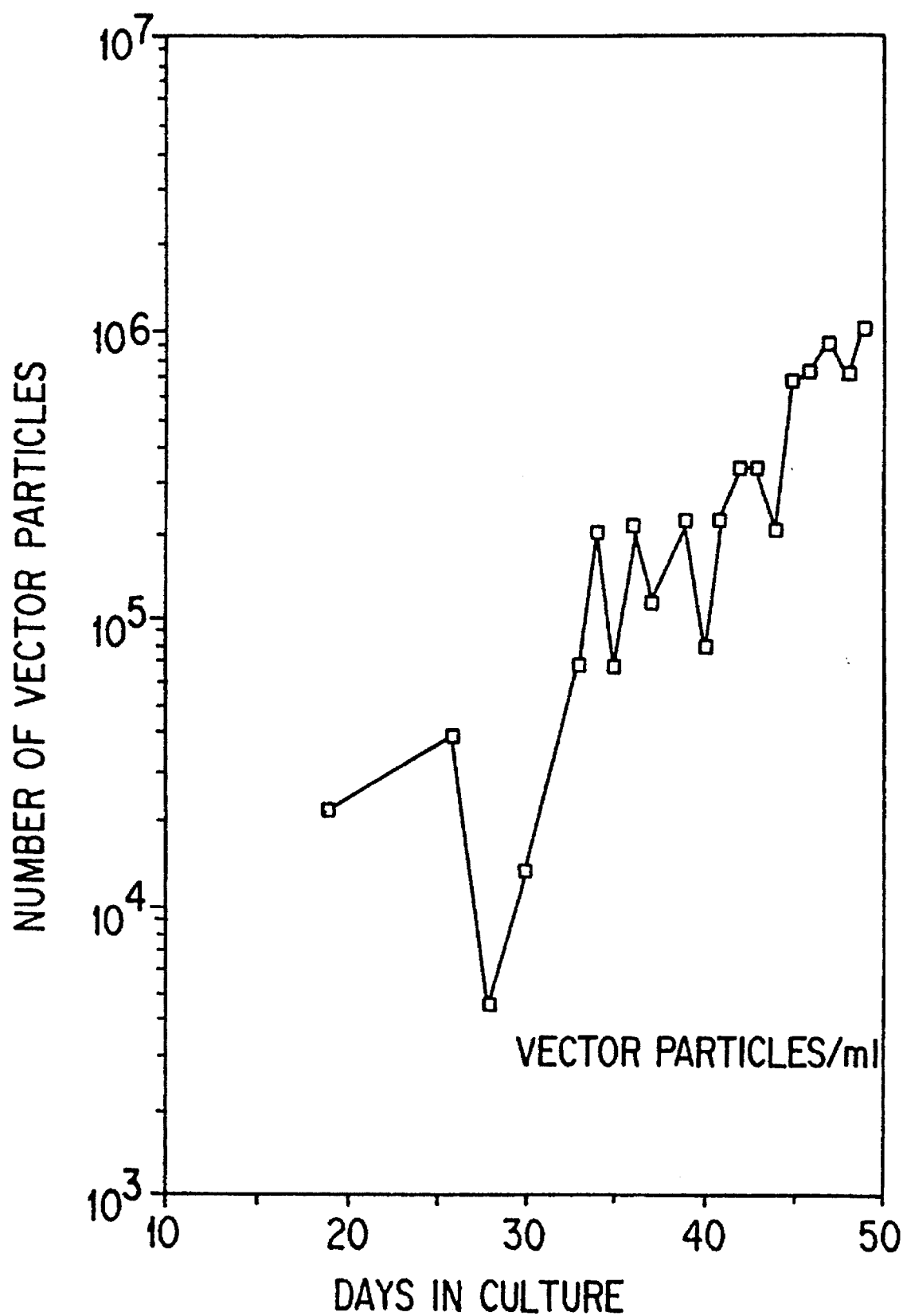
FIG. 1 presents titer (vector particles/ml) as a function of duration of culture in the bioreactor. After 50 days in culture the titer of viral vector particles plateaued at more than $10^6$ particles/ml.
Figure 2:
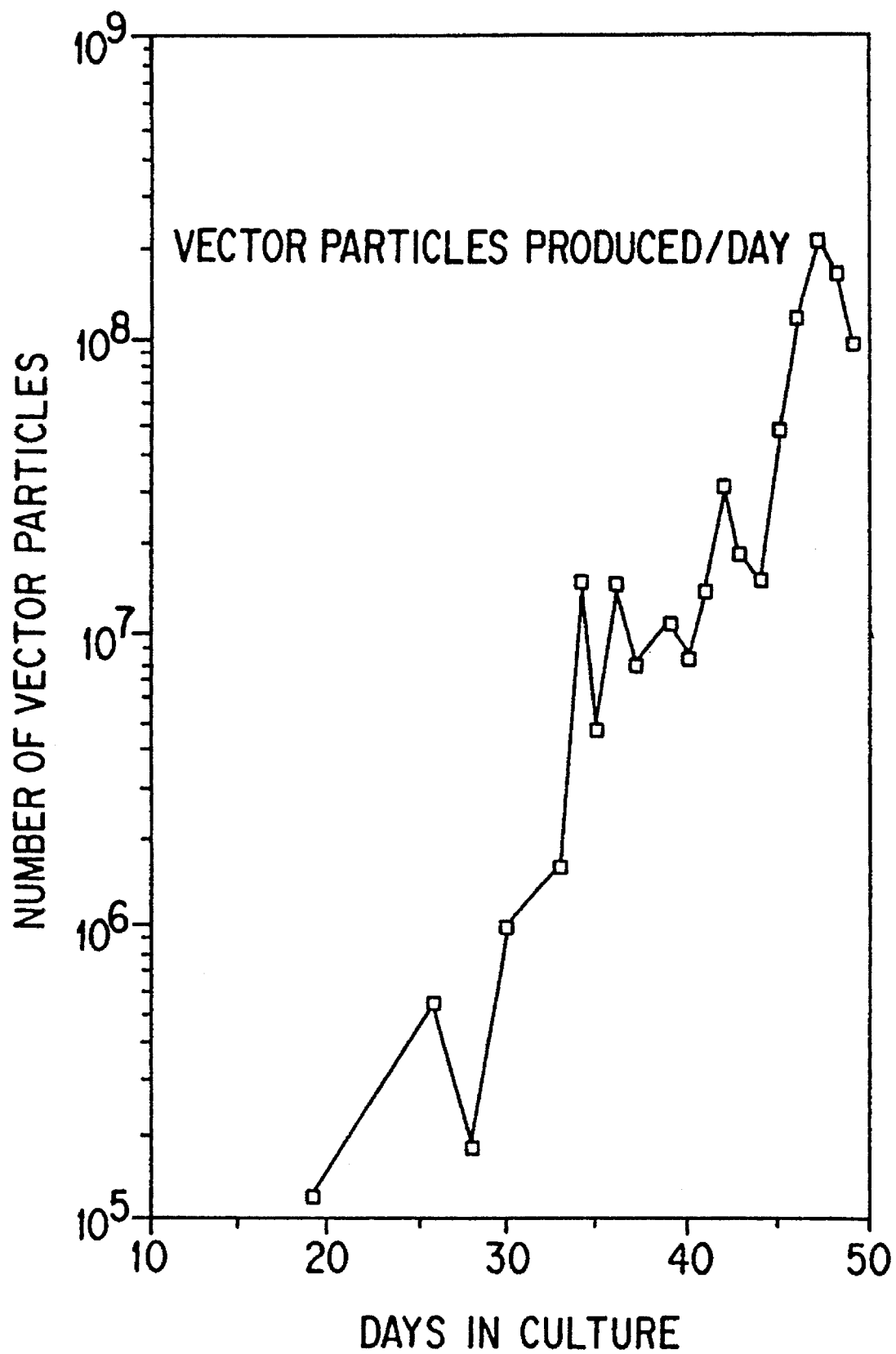
FIG. 2 presents the same data expressed as packaged retroviral vector particle production per day as a function of time in culture. Vector particle production per day increases substantially with duration of the culture.

FIG. 1 presents viral titer as a function of days in culture in the ACS cartridge. FIG. 2 presents the total number of viral particles produced per day as a function of days in culture.

EXAMPLE 2

The effect of harvesting and replacing the ECS on total viral output and viral titer/ml On two successive days, day=t and day=t+1, the EFS medium from a bioreactor, which had been inoculated and incubated as described in Example 1, was harvested and tittered. The ECS was harvested by gently pressurizing one side port bottle through a 0.2 micron filter to force the contents of the ECS out of the bioreactor and into the other side port bottle.

The first ECS harvest, occurring 22.5 hours after the ECS medium was introduced, yielded a titer of $7.0 \times 10^5$ CFU/ml. This was equivalent to a production rate of $5.2 \times 10^7$ virus particles per day. After the harvest in which all of the ECS medium was removed, fresh medium was added to the ECS and incubation was continued for another 4 hours, after which all of the ECS medium was harvested and tittered. This titer was $2 \times 10^5$, which is equivalent to production rate of $12.0 \times 10^7$ particles per day. All remaining ECS medium was removed and completely replaced by fresh medium. The ECS medium was then harvested after 17 hours and completely replaced with fresh medium, which was harvested after 7 hours. The results are shown in TABLE I.

It was possible to achieve viral tilers of $10^5$–$10^6$ and viral production rates from a single bioreactor of more than $10^8$ viral particles per day. Furthermore, increasing the frequency of the ECS harvest appeared to increase total viral output.

For comparison, two T-150 flasks containing a preconfluent monolayer (about $10^7$ cells) of LASN-producing PA317 cells were incubated at $37°$ C. in a humidified 5% $CO_2$ atmosphere. When the cells were confluent, the medium from the monolayer cultures was harvested and tittered. The results, which are presented in TABLE II, demonstrated that in monolayer culture, it was only possible to achieve a titer in the range of about $10^3$ particles/ml.

TABLE I

Production of Viral Particles in the ACS cartridge

| Consecutive Samples | Duration (hours)* | titer × $10^{-5}$** | ECS volume | rate of virus production × $10^{-7}$*** |
|---|---|---|---|---|
| 1 | 22.5 | 7.0 | 70 | 5.2 |
| 2 | 4.0 | 2.0 | 100 | 12.0 |
| 3 | 17.0 | 5.0 | 75 | 5.3 |
| 4 | 7.0 | 8.9 | 70 | 21.3 |

*hour between replacing and harvesting the ECS
**titer = recombinant viral particles/ml
***rate of recombinant viral particle production = recombinant viral particles/ml/day × ECS medium volume

TABLE II

Production of Viral Particles in Monolayer Culture

| Flask #/ Harvest # | Duration (hours)* | titer × $10^{-3}$** | vol (ml) | rate of virus production × $10^{-5}$*** |
|---|---|---|---|---|
| 1/1 | 29 | 1.67 | 92 | 1.27 |
| 1/2 | 27 | 1 | 90 | .80 |
| 2/1 | 29 | 1.11 | 92 | .84 |
| 2/2 | 27 | .56 | 90 | .44 |

*hour between feeding and harvesting all of the medium in the flask
**titer = recombinant viral particles/ml
***rate of recombinant viral particle production = recombinant viral particles/ml/day × volume of supernatant

EXAMPLE 3

Transduction of lymphocytes with the retroviral particles

A LASN-producing PA317 culture was initiated by inoculating a B3 bioreactor (Cellco Advanced Bioreactors, Inc. Kensington, MD.) with $8.4 \times 10^8$ cells, which were 100% viable. The B3 cartridge is similar to the B4 cartridge, except that it smaller. The EFS has a volume of about 50 ml. Tri-lumen, thin-walled tubing was used to connect the cartridge outlet to reservoir in order to increase oxygen transport into the medium. The direction of perfusion of medium was periodically reversed as described in PCT International Application No. WO 90/01271.

The B3 bioreactor was perfused with DMEM that contained 10% heat-inactivated FCS, 2 mM glut amine (Flow Laboratories), 50 units of penicillin/ml and 50 μg streptomycin/ml. The unit was placed in the incubator, as described in Example 1, and the cells were permitted to attach for about 15 minutes. Perfusion was commenced at a low flow rate, less than 100 ml/min. and gradually increased to 300 ml/min. The EFS was harvested periodically as described in Example 2 and centrifuged at about 800×g for about 10 min. to remove cells and cell debris. The harvested EFS was stored at $-70°$ to $-80°$ C. for later analysis.

About five weeks after the culture was initiated, about 60 ml was harvested from the ECS and replaced with fresh medium. About 10 ml of the harvested ECS was removed, diluted and checked for bacterial contamination, which was absent, and to check the cells, which appeared healthy.

The remaining 50 ml. was filtered through a 1 μ pore size nylon Polydisc™ AS filter (WHATMAN Ltd., Maidstone, England). This filtrate was used for transduction of the target cells.

The selected target cells were a human T cell lymphotropic virus I (HTLV I)-transformed, ADA-deficient, IL-2-dependent, human lymphocyte cell line, TJF-2. TJF2 was originally obtained from a patient having ADA deficiency and was then transformed with HTLV I.

A second bioreactor, a B4 bioreactor (Cellco Advanced Bioreactors, Inc., Kensington, Md.) was inoculated with $1.3 \times 10^8$ TJF-2 cells. The cells were cultured in the bioreactor in RPMI 1640 tissue culture medium (Biofluids, Rockville, Md.) supplemented with 10% heat inactivated FCS, penicillin, streptomycin, 2 mM glut amine (Flow Laboratories) and 1000 units/ml of interleukin-2 (IL-2) (provided by Cetus Corp., Emeryville, Calif.). 1000 units/ml of IL-2 were also included in the ECS. The medium in the reservoir was changed every 1–4 days. Also, more TJF-2 cells were periodically injected into the ECS in order to increase cell density. After the culture was established, $7.2 \times 10^8$ cells were removed in a laminar flow hood, by giving the bioreactor cartridge a single gentle shake. About 30–40% of cells were then drained into a side port bottle. The cells were about 65% viable. About 20% of the cells were removed to serve as non-transduced controls. The remaining cells were pelleted and resuspended in 45 ml of the LASN filtrate, described above.

The ECS of the second bioreactor, which contained the remaining TJF-2 cells, was reinoculated with the resuspended cells. RPMI 1640 complete medium, prepared as described above, was added to fill the ECS, the unit was placed in the incubator and perfusion was started. After 2 days, the transduction procedure was repeated with a second volume of LASN filtrate. After two more days, the transduction procedure was repeated again. Before each transduction with LASN, samples of the cells were removed for analysis. The culture was terminated after about 8 days. It contained a total of $1.02 \times 10^{1°}$ cells with 82% viability.

Some of the sample transduced cells were introduced into soft agar and cultured in the presence of G-418. Colony formation indicated that the cells were expressing the neo gene that is present in the LASN vector.

In addition, samples of TJF-2 cells taken from the second bioreactor before transduction, two days after the first transduction and two days after the second transduction were assayed for the presence of the neo gene by polymerase chain reaction (PCR) analysis, which demonstrated the presence of the gene after transduction.

PCR analysis was carried using the GeneAmpR Reagents and DNA Thermal Cycler (Perkin Elmer Cetus, Emeryville, Calif.). DNA was isolated from the transduced and non transduced TJF-2 cells and PCR was initiated with 1–2 μg of genomic DNA with neo gene primers.

The reaction mixture was heated at 94° C. for 2 min., annealed at 56° C. for 2 min, and extended at 72° C. for 3 minutes in the DNA Thermal Cycler for 30 repetitive cycles. The products of the reaction were run on a gel and probed with a neo-specific probe. Genomic DNA from the transduced cells included neo DNA; whereas the non transduced cells did not. Therefore, the target cells are transduced by LASN and have LASN-derived DNA incorporated into genomic DNA.

EXAMPLE 4

Transduction of primary, non-transformed, ADA-deficient lymphocytes with LASN using a dual perfusion bioreactor circuit A B3 cartridge, prepared as described in Example 1, was inoculated with $3.5 \times 10^8$ primary, non-transformed, ADA-deficient lymphocytes, and suspended in 84 ml of the continuously harvested LASN-containing ECS medium. The LASN-containing ECS medium had been harvested during the previous 48 hrs and supplemented with 1000 units of IL-2/ml (Cetus, Emeryville, Calif.). The bioreactor was perfused overnight with AIM-V containing 1000 U IL-2/ml in the forward direction at a rate of about 100 ml/min.

The ECS of the first bioreactor, which contained the LASN-producing PA317 cells, was then connected to the ECS of the target cell bioreactor in the arrangement of a dual perfusion circuit as shown in FIG. 2. A peristaltic pump pumps fresh medium, DMEM medium containing 10% FCS (HyClone, Logan, UTAH) and 1000 units/ml IL-2, into the entrance side port in the first bioreactor. The peristaltic pump was run for 1 minute every hour. The fresh medium was pumped into the ECS at a rate of 5 mls/min. The LASN-producer PA317 cartridge is perfused with DMEM that contains 2 % FCS at a rate of 300 ml/min. As result of the relatively high flow rate of the perfusate and intermittently open side ports, some of the perfusate was ultrafiltered into the ECS through the fiber walls at an approximate rate of about 5 ml/min. Since serum proteins do not ultra filter to a significant extent, the final concentration of FCS proteins in the ECS is estimated to be about 5 % FCS. When fresh ECS medium is not being pumped into the side ports, the perfusate is not ultra filtered.

The pinch clamp that separates the ECS of the two bioreactors automatically closes when the pump is off. A RC-50 Pall filter (Pall Biomedical Products Corp., Glen Cove, N.Y.), which is a leukocyte removal filter for blood, is interposed between the first bioreactor and the clamp in order to remove any LASN-producing cells that might be dislodged from the ECS of the bioreactor that contains the LASN-containing ECS medium.

The two bioreactors were sterilely attached using a Sterile Tubing Welder (SCDIIB, DuPont, Wilmington, Del.). One side port of the second bioreactor is connected to the input from the ECS of the first bioreactor and the other is connected to a flask, which collects the overflow.

About $3.5 \times 10^8$ lymphocytes were inoculated into the second bioreactor and perfused overnight with AIM-V that contained 1000 units/ml of IL-2 at a rate of about 50 ml/min that reversed direction every minute. Because the flow rate of the perfusate in the second bioreactor was relatively slow, there was no substantial ultrafiltration into the overflow flask.

About 19 hours after the second bioreactor was inoculated, the peristaltic pump, which was pumping at a rate of about 5 ml/min, was turned on for one minute and about 10 ml of the ECS medium from the first bioreactor was introduced into the ECS of the second bioreactor. The 10 ml includes 5 ml of fresh medium from the reservoir and 5 ml resulting from the ultrafiltration of the perfusate into the ECS that occurs by virtue of the relatively high flow rate of the perfusate. Incubation was continued and once an hour the peristaltic pump was automatically turned on for 1 minute. After about 87 hours in culture, including the initial 19 hours, approximately $0.5 \times 10^8$ lymphocytes from the second bioreactor were harvested by draining them from the ECS.

At the same time, the second bioreactor was inoculated with the lymphocytes, $2 \times 10^6$ lymphocytes were introduced into each well of two 24 well Costar™ plates. Prior to introduction into the plates, the lymphocytes had been suspended in 1 ml of the continuously harvested LASN-containing ECS medium, which was harvested as described in Examples 1 and 2. Then 1 ml of AIM-V containing 2000 units/ml of IL-2 was added to each well. The cells were incubated in a $CO_2$ incubator at 37° C. for 87 hours. About $1.6 \times 10^8$ cells were harvested from the plates at the same time the lymphocytes in the second bioreactor were harvested.

Aliquots of about $10^7$ lymphocytes from both the plates and bioreactor were placed in centrifuge tubes, pelleted at 800×g for 10 min, washed in Hanks BSS, re-pelleted and frozen at −80° C. for subsequent ADA protein analyses.

EXAMPLE 5

Measurement of ADA production by the transduced lymphocytes

Samples of lymphocytes prepared in Example 4 were assayed for ADA production. The cell pellets were warmed and lysed by freeze-thawing. $^{14}$C-adenosine, an ADA substrate, was added and the mixture was incubated at 37° C. for 1 hr, heat at 95° C. for 5 min to quench the reaction. The mixture is centrifuged and aliquots are spotted onto thin layer chromatography (TLC) paper and run in solvent containing Na-phosphate, saturated ammonium sulfate and N-propylalcohol for 1 hr. The TLC paper dried overnight. The spots are cut-out and placed scintillation vials with scintillation fluid and counted in a scintillation counter.

The rate of ADA production by the singly transduced lymphocytes grown in the 24 well plates was 55.2 nmoles/min/$10^8$ lymphocytes. ADA production by the continuously transduced lymphocyte cells harvested from the second bioreactor was 73.2 nmoles/min/$10^8$ lymphocytes. This rate of ADA production is comparable to the rate of ADA production, 50–90 nmoles/min/$10^8$ lymphocytes, by normal lymphocytes that are not deficient in ADA production.

In comparison, the rate of ADA production by lymphocytes transduced using the supernatant obtained from LASN-producing PA317 cells grown in monolayer and exposed to the supernatant six times was only 11.6 nmoles/min/$10^8$ lymphocytes. The ADA activity of the non-transduced lymphocytes from the ADA-deficient patient was 0.6 nmoles/min/$10^8$ lymphocytes.

EXAMPLE 6

High titer serum-free production of LNL6 retroviral particles in an ACS cartridge Methods LNL-6 producer cells (PA-317; ATCC Accession No. CRL 9078) are capable of secreting packaged LNL-6 virions. PA317 packaging cells were originally derived from thymidine kinase-negative (TK$^-$) NIH 3T3 cells by cotransfection with retrovirus packaging construct DNA (pPAM3) and the herpes simplex virus thymidine kinase (TK) gene. The construction of the PA317 packaging cells is described in Miller et al., *Biotechniques* 7: 980 (1989); Miller et al., *Mol. Cell. Biol.* 6:2895–2902 (1986); and Miller, D., U.S. Pat. No. 4,861,719). NIH 3T3 (TK$^-$) cells are described in J. Virol. 39:935–944 (1981). The LNL-6 retrovirus contains the Neomycin-resistance gene (Neo$^R$) and is described in Bender et al., *J. Virol.* 61:1639 (1987). LNL-6 is a derivative of the retroviral vector N2 (*Nature* 318:149–154 (1985)). Thus, LNL-6 producer cells were constructed using publicly available and well known starting materials.

The LNL-6 producer cell cultures were initiated in 25 cm$^2$ flasks using DMEM/10 (DMEM containing 10% fetal bovine serum (FBS)). Once the cultures reached near confluence, the cells were trypsinized, resuspended in DMEM/10, and at least $4.0 \times 10^7$ of the packaging cells were inoculated into the extra capillary space (ECS) of an artificial capillary system (ACS) cartridge. Prior to inoculating the LNL6-packaging cells, the ACS cartridge was perfused with approximately 100 ml AIM-V for 2 or more days at 34° C. L-lactate production in the ACS was monitored daily using an YSI glucose/lactate automated analyzer (Yellow Springs Instrument Co., Inc.). Briefly, the daily L-lactate production was calculated by dividing the change of total lactate content by the day between measurements, plotting the rate of lactate production, and determining the doubling time of lactate production based on logarithmic growth rate. When the L-lactate production rate reached more than 60 mg/day, the extracapillary medium was harvested daily. When the L-lactate production rate was consistently over 100 mg/day, the extracapillary medium was replaced with fresh AIM-V. Irrespective of whether DMEM/10 or AIM-V was present in the ECS, the perfusion medium (i.e., the culture medium used to perfuse the ACS capillaries) was always AIM-V. Retroviral suspensions were harvested from the ECS approximately four to six times per week and stored at −70° C. until infectivity tilers were assessed using a colony forming assay with 80% confluent 3T3 cell cultures in 6-well plates.

For comparative purposes, LNL6 producer cells were grown to confluence in flask cultures using DMEM/10 as the culture medium. Retroviral suspensions were harvested from the confluent cultures approximately four to six times per week for two weeks and stored at −70° C. until infectivity liters were assessed using a colony forming assay with 80% confluent 3T3 cell cultures in 6-well plates.

Briefly, colony forming assays were performed as follows: Low passage number (<10) NIH/3T3 cells were plated in 6-well plates at $1.0 \times 10^5$ cells per well in 2.0 ml DMEM/10 and incubated overnight at 37° C. The plating medium was removed and 2.0 ml serial 10-fold dilutions of LNL-6 supernatant, diluted in DMEM/10 containing 8.0 µg/ml polybrene (hexadimethrine bromide, Sigma), were added to triplicate wells of 3T3 cells and incubated overnight at 32° C. The diluted inoculum was removed, replaced with 3.0 ml DMEM/10 containing 0.8 mg/ml G418 (Gentecin, GIBCO), and incubated at 37° C. for 8–10 days until colonies could be seen. The medium was once again removed, the wells washed once with 3.0 ml PBS, and stained with 0.6% methylene blue in methanol. Plates were washed with water and allowed to dry. Colonies were then counted. A stock retroviral supernatant of known tiler was included in all cfu assays to control for assay variability. Results were calculated as follows: cfu/ml=average colonies×(1/dilution of supernatant). Example: 20 colonies per well×(1/$10^6$)=2.0× $10^7$ cfu/ml.

Results

Retroviral suspensions obtained from ACS cartridges contained extraordinarily high titers of LNL-6 retroviral vector in both serum-containing and serum-free ECS medium. FIG. 4 shows the infectivity titers of LNL-6 (the bar graphs) produced in an ACS cartridge at 34° C. as assessed by the colony forming assay described above. At day 15 of culture, the DMEM/10 in the ECS was replaced with fresh AIM-V. Retroviral suspension samples were taken every 24, 48, or 72 hours for the colony forming assay. These data demonstrate that an ACS cartridge can sustain high titer production of packaged and infectious LNL6 in serum-free medium at 34° C. Also provided in FIG. 4 is a measurement of L-lactate production (connected triangles) at the indicated intervals during culture. L-lactate production is a measure of cellular growth. Thus, these data demonstrate that an ACS cartridge can support the growth of the LNL6-producer cells in serum-free medium at 34° C.

FIG. 5 shows the infectivity titers of LNL-6 (the bar graphs) produced in an ACS cartridge at 37° C. as assessed by the colony forming assay described above. At day 7 of culture, the DMEM/10 in the ECS was replaced with fresh AIM-V. At day 12 of culture, the AIM-V in the ECS was replaced with DMEM/10 which was in turn again replaced with AIM-V on day 13. Retroviral suspension samples were taken after 24, 48, or 72-hours for the colony forming assay. These data demonstrate that an ACS cartridge can sustain high titer production of packaged and infectious LNL6 in serum-free medium at 37° C. Also provided in FIG. 5 is a measurement of L-lactate production (connected triangles) at the indicated intervals during culture. L-lactate production is a measure of cellular growth. Thus, these data demonstrate that an ACS cartridge can support the growth of the LNL6-producer cells in serum-free medium at 37° C.

As discussed above, for comparative purposes, LNL6-infectivity titers were also assessed for flask cultures using DMEM/10 as the culture medium by taking retroviral suspension samples after 24, 48, or 72 hours and assaying infectivity titers in the colony forming assay. The results are shown below in Table III.

TABLE III

LNL-6 Production in Artificial Capillaries Compared to Production in Flasks

| Culture Type | Temp. (°C.) | ECS Medium[1] | Samples Tittered (n) | Average Titer (× $10^{-6}$ cfu/ml) | Fold Increase versus Flask |
| --- | --- | --- | --- | --- | --- |
| Flask | 37 | — | 4 | 0.76 | 1.0 |
| ACS | 37 | DMEM/10 | 4 | 3.3 | 4.3 |
| ACS | 37 | AIM-V | 8 | 3.1 | 4.1 |
| Flask | 34 | — | 1 | 1.25 | 1.0 |
| ACS | 34 | DMEM/10 | 8 | 21.6 | 17.3 |
| ACS | 34 | AIM-V | 2 | 58.5 | 46.8 |

[1]Indicates medium in extracapillary space only. All artificial capillary cultures were perfused with AIM-V. All flask cultures were grown in DMEM/10.

Flask cultures in serum-containing medium at 37° C. produced an average of $0.76 \times 10^6$ cfu/ml of packaged and infectious LNL6. ACS cultures in serum-containing medium at 37° C. produced an average of $3.3 \times 10^6$ cfu/ml of packaged and infectious LNL6. This is a 4.3-fold increase over that achieved in the serum-containing flask cultures. ACS cultures in serum-free medium at 37° C. produced an average of $3.1 \times 10^6$ cfu/ml of packaged and infectious LNL6. This is a 4.1-fold increase over that achieved in the serum-containing flask cultures.

Flask cultures in serum-containing medium at 34° C. produced an average of $1.25 \times 10^6$ cfu/ml of packaged and infectious LNL6. ACS cultures in serum-containing medium at 34° C. produced an average of 21.6 cfu/ml of packaged and infectious LNL6. This is a 17.3-fold increase over that achieved in the serum-containing flask cultures. ACS cultures in serum-free medium at 34° C. produced an average of 58.5 cfu/ml of packaged and infectious LNL6. This is a 46.8-fold increase over that achieved in flask culture.

These data indicate that ACS cultures of LNL6-producer cells in serum-free medium produce comparable (at 37° C.) or increased (at 34° C.) titers of packaged and infectious retrovirus vector as compared to ACS cultures of LNL6-producer cells in serum-containing medium. Thus, high titers of LNL-6 suspensions were harvested repeatedly from ACS cartridges in both serum-containing and serum-free medium. Moreover, the titers achieved from ACS cartridges in both serum-containing and serum-free medium were significantly higher than titers achieved in flask culture. The "Samples Tittered" column in Table III represents retroviral suspension supernatants taken after 24, 48, or 72 hours of culture. To ensure the data were meaningful, the culturing time of samples taken from the ACS cartridge were always equal to or less than the culturing time of the corresponding sample taken from the flask culture. Thus, the "Fold Increase" of ACS-produced LNL-6 verses flask produced LNL-6 is actually greater than that shown in Table III.

Summary

Artificial capillary cartridges provided appropriate microenvironments for the adaptation of the packaging cell line to serum-free medium and subsequent high-titer retroviral production. The highest titers were obtained from cultures grown in ACS cartridges at 34° C. The overall average titers of LNL6 suspensions produced in ACS cartridges are shown below in Table IV.

TABLE IV

Results Sumary

| ECS Medium | Average Titer (cfu/ml) | Highest Titer (cfu/ml) |
| --- | --- | --- |
| DMEM/10 | $1.59 \times 10^7$ | $7.23 \times 10^7$ |
| AIM-V | $1.24 \times 10^7$ | $6.07 \times 10^7$ |

From Table IV above, it is clear that high titers of LNL-6 were harvested repeatedly from ACS cartridges in both serum-containing and serum-free medium. Flask cultures of LNL-6 in DMEM/10 averaged $0.86 \times 10^6$ cfu/ml, levels typical for this vector. The highest titer of retrovirus produced in a flask ($1.7 \times 10^6$ cfu/ml) was a 72 hour supernatant grown at 37° C.

While these data are not shown here, artificial capillary-produced LNL-6 (in serum-free medium) successfully transduced fresh, normal peripheral blood lymphocytes in vitro using conventional techniques as evidenced by the presence of $Neo^R$ gene product in the transduced cells after expansion in culture. Thus, we have demonstrated that 3T3 cells (mice fibroblasts) (see the colony forming assay discussion above) and peripheral blood lymphocytes can be transduced using conventional techniques with ACS capillary-produced (in serum-free medium) LNL-6 retroviral vectors.

EXAMPLE 7

LNL-6 Production in flasks using serum-free or reduced-serum culture medium

The following experiment was performed to determine whether flask culture could support the serum-free or reduced-serum production of LNL6.

Methods

LNL-6 producer cells were inoculated in various media into 25 cm² flasks. In particular, LNL-6 cells were thawed from frozen stock and $2 \times 10^6$ of the cells were inoculated into each of four 25 cm² flasks at $0.2 \times 10^6$/ml with the following media: (1) DMEM/10% fetal bovine serum (FBS); (2) DMEM/10% pooled human plasma (PHP); (3) AIM-V/5% PHP; and (4) Macrophage-SFM (M0-SFM)/5% PHP. All cultures were grown in humidified 5% $CO_2$ in air at 34° C.

Results

Two days after the initiation of the flask cultures, the cells in all conditions except DMEM/10% FBS were dead. This agrees with the Pironin et al. (*Int. J. Cancer* 51:980–988 (1992)) finding that murine NIH 3T3 cells are unable to grow autonomously in serum-free medium. The one surviving flask with DMEM/10% FBS was trypsinized. $1 \times 10^6$ of the cells were harvested and inoculated into each of three 25 cm$^2$ flasks containing 10%, 3.2%, and 1.0% FBS in DMEM. Three days later the cells in 10% FBS were approximately 70% confluent, the cells in 3.2% FBS were approximately 25% confluent, and the cells in 1.0% FBS were <5% confluent with many dead cells. The cells in 3.2% FBS reached confluence 5 days after inoculation. The cells grown in 1.0% FBS never reached more than 5% confluence. Supernatants were harvested 72 hours after inoculation and twice again 24 hours after fresh medium was placed onto the flasks. LNL-6 infectivity titers of the supernatants was performed using the colony forming assay described above. The LNL-6 titers are shown below in Table V.

TABLE V

LNL-6 Production in Flasks at 34° C. in Various Media Supplemented with FBS or Pooled Normal Human Plasma

| days post-inoculation | hours post-feed | DMEM + FBS (%) | LNL-6 titer (cfu/ml) |
|---|---|---|---|
| 2 | 48 | 10.0 | $1.6 \times 10^5$ |
| 5 | 72 | 10.0 | $3.6 \times 10^5$ |
| 5 | 72 | 3.2 | $7.7 \times 10^3$ |
| 5 | 72 | 1.0 | $<1.0 \times 10^3$ |
| 7 | 24 | 10.0 | $3.4 \times 10^5$ |
| 7 | 24 | 3.2 | $3.0 \times 10^4$ |
| 7 | 24 | 1.0 | $<1.0 \times 10^3$ |
| 9 | 24 | 3.2 | $6.7 \times 10^4$ |

Since modifications will be apparent to those of skill in the art, it is intended that this invention be limited only by the scope of the appended claims. The disclosure of all references, patent applications and patents recited herein are hereby incorporated by reference.

We claim:

1. A method for the production of packaged retroviral vectors, comprising:

(a) inoculating PA-317 derived packaging cells which produce packaged and infectious retroviral vectors into an artificial capillary system (ACS) cartridge;

(b) culturing said packaging cells in the presence of bovine serum-containing culture medium;

(c) replacing said bovine serum-containing culture medium with bovine serum-free culture medium; and (d) culturing said packaging cells in the presence of said bovine serum-free culture medium to achieve packaged and infectious retroviral vectors.

2. The method of claim 1 wherein said culturing occurs for a sufficient amount of time to produce high titers of packaged and infectious retroviral vectors.

3. The method of claim 1, wherein said retroviral vectors encode a therapeutically effective product.

4. The method of claim 1, wherein said recombinant retroviral vector is LNL-6.

5. The method of claim 1, further comprising:

(e) collecting supernatant containing said packaged and infectious viral vectors from said ACS cartridge.

6. The method of claim 1, wherein said bovine serum-free culture medium is AIM-V.

* * * * *